(12) United States Patent  
Russell

(10) Patent No.: US 8,080,798 B2
(45) Date of Patent: Dec. 20, 2011

(54) GAS MEASUREMENT SYSTEM

(75) Inventor: James T. Russell, Bellevue, WA (US)

(73) Assignee: RIC Investments, LLC, Wilmington, DE (US)

(*) Notice: Subject to any disclaimer, the term of this patent is extended or adjusted under 35 U.S.C. 154(b) by 0 days.

(21) Appl. No.: 12/371,151

(22) Filed: Feb. 13, 2009

(65) Prior Publication Data

US 2009/0146062 A1 Jun. 11, 2009

Related U.S. Application Data

(63) Continuation of application No. 11/368,832, filed on Mar. 6, 2006, now Pat. No. 7,501,630, which is a continuation-in-part of application No. 11/165,670, filed on Jun. 24, 2005, now Pat. No. 7,432,508, which is a continuation-in-part of application No. 10/792,180, filed on Mar. 3, 2004, now Pat. No. 7,183,552, and a continuation-in-part of application No. 10/781,382, filed on Feb. 18, 2004, now Pat. No. 6,954,702.

(60) Provisional application No. 60/449,428, filed on Feb. 21, 2003, provisional application No. 60/452,656, filed on Mar. 7, 2003.

(51) Int. Cl.
*G01J 5/08* (2006.01)
(52) U.S. Cl. ........................................... 250/343
(58) Field of Classification Search ................... 250/343
See application file for complete search history.

(56) References Cited

U.S. PATENT DOCUMENTS

| | | | |
|---|---|---|---|
| 3,614,431 A | 10/1971 | Low | |
| 4,177,381 A | 12/1979 | McClatchie | |
| 4,546,778 A | 10/1985 | Sullivan | |
| 4,692,621 A | 9/1987 | Passaro | |
| 4,899,053 A | 2/1990 | Lai | |
| 4,907,166 A | 3/1990 | Corenman | |
| 4,914,720 A | 4/1990 | Knodle | |
| 4,958,075 A | 9/1990 | Mace | |
| 5,058,601 A | 10/1991 | Riker | |
| 5,282,473 A | 2/1994 | Braig | |
| 5,464,982 A | 11/1995 | Drucker | |
| 5,793,044 A | 8/1998 | Mace | |
| 6,632,402 B2 | 10/2003 | Blazewicz | |
| 6,709,405 B2 | 3/2004 | Jonson | |
| 6,828,910 B2 | 12/2004 | VanRyzin | |
| 2002/0029003 A1* | 3/2002 | Mace et al. | 600/532 |
| 2002/0098120 A1 | 7/2002 | Blazewicz | |
| 2003/0190262 A1 | 10/2003 | Blazewicz | |
| 2003/0191405 A1 | 10/2003 | Rich | |
| 2004/0013570 A1 | 1/2004 | Labuda | |
| 2004/0069304 A1 | 4/2004 | Jam | |
| 2004/0256560 A1 | 12/2004 | Russell | |
| 2004/0267151 A1 | 12/2004 | Eckerbom | |

OTHER PUBLICATIONS

Perkin Elmer Optoelectronics, "Digital Mainstream CO2 Sensor", 2001.

* cited by examiner

*Primary Examiner* — David Porta
*Assistant Examiner* — Marcus Taningco

(57) ABSTRACT

A gas measurement system includes a housing adapted to be mounted on an airway adapter, and a luminescence quenching gas measurement assembly disposed in the housing. The luminescence quenching gas measurement assembly includes a source disposed in a first plane, and at least one detector also disposed in the first plane.

21 Claims, 23 Drawing Sheets

GAS MEASUREMENT SYSTEM

CROSS-REFERENCE TO RELATED APPLICATIONS

This application is a Continuation under 35 U.S.C. §120 of U.S. patent application Ser. No. 11/368,832, filed Mar. 6, 2006, which is a Continuation-In-Part under 35 U.S.C. §120 from U.S. patent application Ser. No. 11/165,670 filed Jun. 24, 2005, now U.S. Pat. No. 7,432,508, which is (a) a Continuation-In-Part under 35 U.S.C. §120 from U.S. patent application Ser. No. 10/792,180, filed Mar. 3, 2004, which claims priority under 35 U.S.C. §119(e) from provisional U.S. patent application Ser. No. 60/452,656 filed Mar. 7, 2003, and is also (b) a Continuation-In-Part under 35 U.S.C. §120 from U.S. patent application Ser. No. 10/781,382, filed Feb. 18, 2004, now U.S. Pat. No. 6,954,702, which claims priority under 35 U.S.C. §119(e) from provisional U.S. patent application Ser. No. 60/449,428 filed Feb. 21, 2003, the contents of each of these applications are incorporated herein by reference.

BACKGROUND OF THE INVENTION

1. Field of the Invention

The present invention relates to a mainstream respiratory gas measurement system with integrated signal processing and improved optical design, and to a method of assembling such a system.

2. Description of the Related Art

Respiratory gas measurement systems comprise gas sensing, measurement, processing, communication, and display functions. They are considered to be either diverting, i.e., sidestream, or non-diverting, i.e., mainstream. A diverting gas measurement system transports a portion of the sampled gases from the sampling site, which is typically a breathing circuit or the patient's airway, through a sampling tube, to the gas sensor where the constituents of the gas are measured. A non-diverting or mainstream gas measurement system does not transport gas away from the breathing circuit or airway, but measures the gas constituents passing through the breathing circuit using a gas sensor disposed on the breathing circuit.

Conventional mainstream gas measurement systems include a gas sensing, measurement and signal processing components required to convert the detected or measured signal, for example a voltage, into a value, such as transmittance, that may be used by the system to determine a constituent of a gas being measured. In a conventional mainstream gas measurement system, a gas sensor is coupled to a sample cell that is placed at the breathing circuit. The gas sensor located on the airway adapter disposed in the breathing circuit only includes the components required to output a signal corresponding to a property of the gas to be measured. Placement of the sample cell directly at the breathing circuit results in a "crisp" waveform that reflects in real-time the partial pressure of the measured gas, such as carbon dioxide or oxygen, within the airway. The sample cell, which is also referred to as a cuvette or airway adapter, is located in the respiratory gas stream, obviating the need for gas sampling and scavenging, as required in a sidestream gas measurement system.

For a conventional gas measurement system that is capable of measuring carbon dioxide, the gas sensor includes a source that emits infrared radiation, which includes the absorption band for carbon dioxide. The infrared radiation is emitted in a direction that is normal to the flow path of the respiratory gas stream. Carbon dioxide within the sample gas absorbs the radiation at some wavelengths and passes other wavelengths. The conventional gas sensor includes photodetectors that measure the transmitted radiation.

For gas measurement systems that are capable of measuring oxygen using luminenscence quenching measurement techniques, the gas sensor may include an excitation source that emits visible radiation, which excites a photosensitive chemical disposed on or within a substrate, and a detector, which measures the radiation emitted by the chemical upon exposure to oxygen. The gas concentration may be determined from the time response of the luminescence using known relationships, such as the Stem-Volmer relationship.

A conventional mainstream host system contains the electronics that control the emitter in the gas sensor, and provides the gas measurement functions based on the output signals from the detector. Mainstream gas measurement systems known in the art transmit analog signals along a cable, typically 6 to 8 feet in length, between the host system and the gas sensor and, as such, are susceptible to electromagnetic interference (EMI). This is particularly important given the trend towards requiring compliance with increased electromagnetic immunity levels in international medical device standards. An example of such conventional mainstream gas measurement systems are shown in U.S. Pat. No. 4,914,720 issued to Knodle et al and U.S. Pat. No. 5,793,044 issued to Mace et al.

With the measurement and signal electronics located in the host system, existing mainstream gas measurement systems are complex and costly to interface to host systems. The host system conventionally includes circuitry to perform functions such as (1) creating timing signals; (2) supplying pulsatile power to a solid state infra-red emitter; (3) measuring and precisely controlling the temperature of the infra red detectors; (4) measuring and controlling an airway adapter heater; (5) signal conditioning including filtering and programmable gain setting; and (6) watchdog circuitry to prevent accidental destruction of the infra-red emitter.

Additionally, to be accepted in clinical use, a mainstream gas measurement system must be designed in a robust manner such that it is unaffected by typical mechanical abuse and environmental variations in temperature and humidity. The instrument, or at least the gas measurement system portion of the instrument, must be small and light weight so as to not interfere with the motions of the patient, or with other medical equipment or treatments. In order to achieve the goals of being small and lightweight, the optical portion of the gas measurement system must also be designed such that they occupy as little space as possible and weigh as little as possible.

Given these known complexities of conventional gas measurement systems, it is desirable to provide a mainstream gas measurement system that is small, lightweight, and simpler to interface to host systems. It is also desirable that such a system provide improved methods of assembly over known gas measurement systems.

SUMMARY OF THE INVENTION

Accordingly, it is an object of the present invention to provide an optical bench that overcomes the shortcomings of optical benches of known luminescence quenching based gas measurement systems. This object is achieved according to the present invention by providing a gas measurement system assembly that includes a housing adapted to be mounted on an airway adapter and a luminescence quenching gas measurement assembly disposed in the housing. The luminescence quenching gas measurement assembly includes a radiation source disposed in a first plane, and at least one detector also disposed in the first plane. This configuration provides a relatively compact configuration for the luminescence quenching gas measurement assembly.

It is a still further object to provide a gas measurement system that includes a conduit adapted to carry a flow of gas, a sensing film in communication with the flow of gas in the conduit, and the luminescence quenching gas measurement assembly described in the immediately preceding paragraph.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE EXEMPLARY EMBODIMENTS

A gas measurement system 100 according to the principles of the present invention includes all of the signal and data processing required to produce continuous values of a partial pressure or concentration of a gas flowing through an airway adapter in fluid communication with a patient's airway. The gas measurement system is located on a "measurement head" that fits onto an airway adapter. The gas measurement system includes the electronic circuitry required to measure and compute a continuous value for infrared absorbing gases, such as carbon dioxide, and luminescence quenching gases, such as oxygen, and interface the gas measurement system to a host system. In an exemplary embodiment, gas measurement system 100 acquires and processes the analog signals, then transmits digitized patient parameters and waveforms through an interface cable 120 as a serialized data stream.

The gas measurement system of the present invention eliminates the need for an additional electronics board inside a host system that would otherwise be required to process the signal output from the detector, thus conserving space within the host system and reducing costs to the end user. Through efficiencies in the design and through miniaturization, the resulting gas measurement system is nearly as small and lightweight as existing mainstream gas measurement sensors. The addition of the signal processing without any significant increase in size or weight is particularly important in applications in which the gas measurement system is employed with an airway adapter in close proximity to a patient's face at the distal end of an endotracheal tube or a nasal cannula to monitor a patient's breathing.

Figure 1:
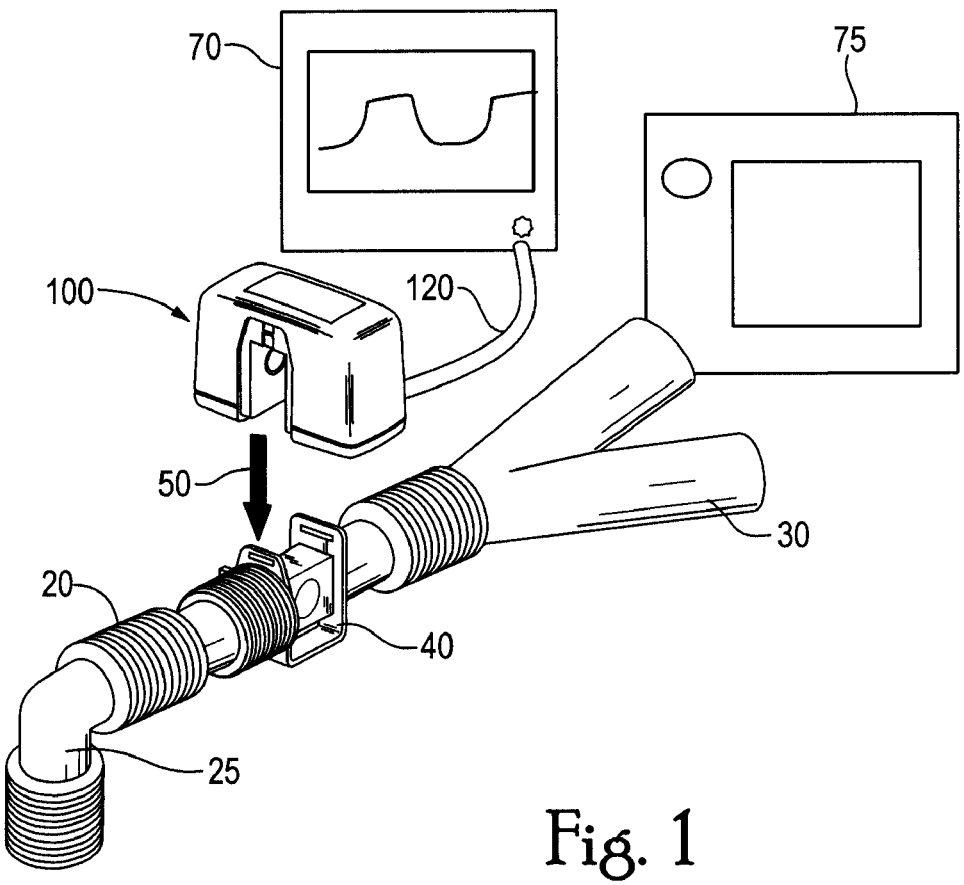
FIG. 1 is a perspective view of a gas measurement system coupled to a host system and configured to be removably secured to an airway adapter assembled with the components of a patient breathing circuit according to the principles of the present invention.
Figure 2:
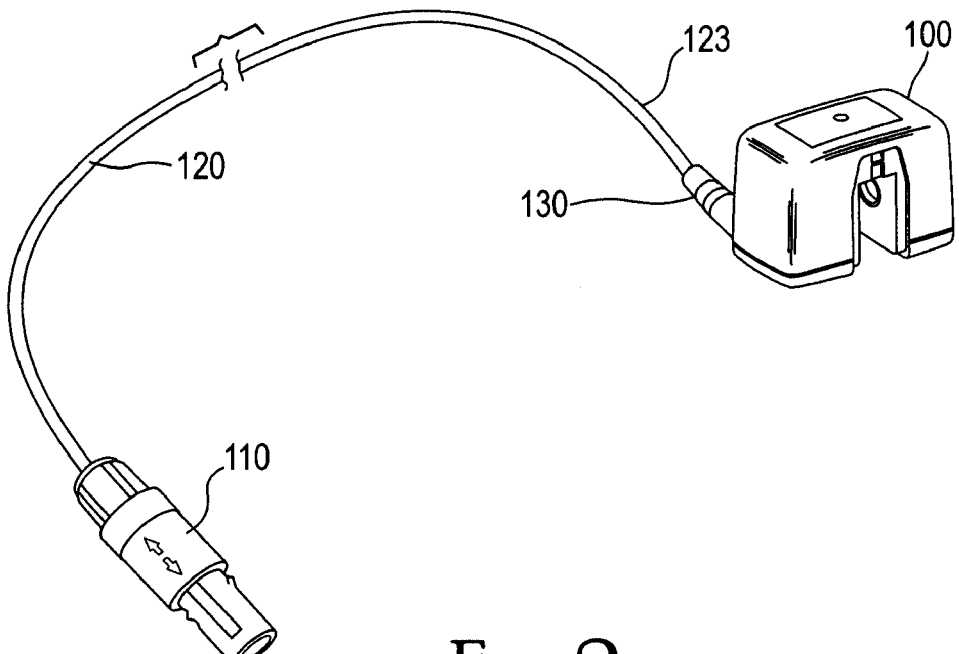
FIG. 2 is a perspective view of the gas measurement system configured to be coupled to a host system.
Figure 3:
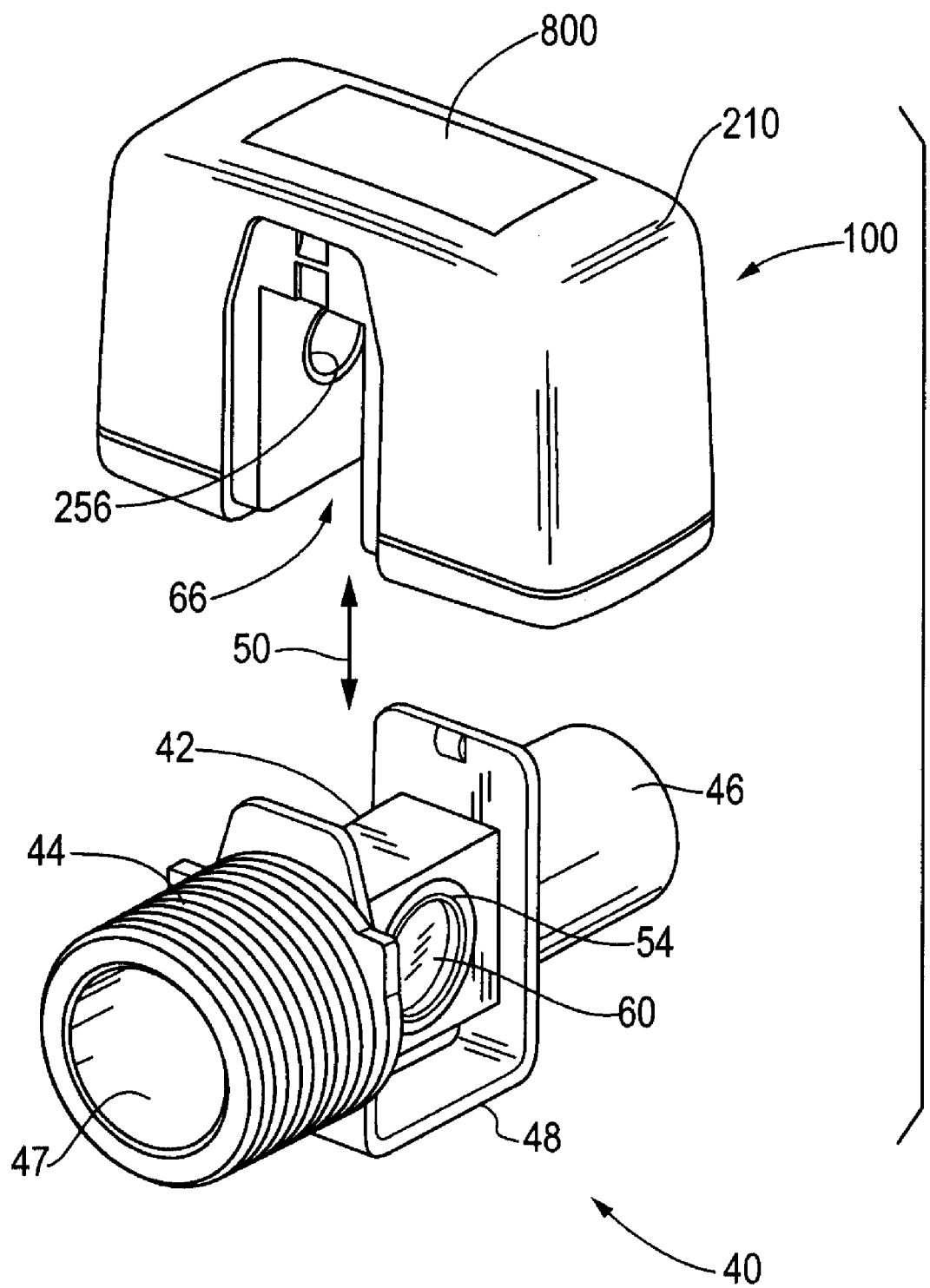
FIG. 3 is a perspective view of the gas measurement system configured to be removably secured to an airway adapter.

An exemplary embodiment of an airway adapter 40 and a gas measurement system 100 constructed in accordance with, and embodying, the principles of the present invention are shown in FIGS. 1-3. Conventional gas measuring systems do not locate the signal processing and control electronics in the gas measurement system, but locate any such feature in the host system. The present invention takes advantage of highly integrated digital signal processing (DSP) technology to perform many of the complex electronic interface functions within a small single chip processor that includes program and data storage as well as analog to digital conversion.

Many of the efficiencies obtained in the integrated respiratory gas measuring system are a consequence of the relocation of the electronics into the gas measurement system. For example, this relocation has affected aspects of the design of interface cable 120, such as the number of conductors, shielding requirements, and consequently the thickness, weight and cost of the cable. The cable requires fewer conductors and so is smaller, lighter, and more flexible providing less load and drag forces on the sensor. The exemplary embodiment uses 7 wires and a shield, whereas conventional devices use 16 wires and two shields.

The present invention has a number of additional advantages over conventional gas measuring systems, including flexibility/simplified interfacing to a host system 70, and increased immunity to radiofrequency interference. With a simplified hardware and software interface, host system 70 only requires a simple and small connector wired to a serial port, and a couple of supply voltages. In clinical application, adding weight to the patient circuit near the ET tube is always of concern, especially for pediatric and neonatal applications. The present invention offers a significant improvement in this regard, because the weight and potential resulting drag of the cable can be reduced. Existing cables to host systems are thicker in diameter, heavier and less flexible.

Conventional gas measurement systems, with components at or near the patients airway, often have difficulty meeting the existing immunity standard of 3 volts/meter. Updates to medical device electromagnetic compatibility international standards have raised this test level to as high as 20 volts/meter. Compliance of these standards with existing designs would be very difficult and expensive because of the susceptibility to interference of analog signals transmitted through a cable. In the present invention, the need to transmit analog signals in the cable to the host system is eliminated and all the components and signals susceptible to RFI are located near the sensing elements in the gas measurement system.

The elimination of the need for all the complex external interface electronics leads to greatly reduced system cost. The efficient use of interconnection technologies, such as rigid-flex circuit boards, and other manufacturing efficiencies result in a total system cost that is lower than the cost of the existing mainstream gas measurement systems alone.

Integration of the measurement and signal processing electronics of the gas measurement system increases the waste heat generated within gas measurement system 100. The compact nature of the design requires careful consideration of the thermal design. For example, gas measurement system 100 is configured to permit the waste heat produced by the emitter and the electronics of the gas measurement system to heat the windows of the airway adapter to reduce fogging. These features of the present invention allow the ceramic heater (also known as the case heater) that has been used in conventional gas measurement systems to be eliminated. Additionally, the elimination of the ceramic heater, along with other efficiencies in the design, have permitted the total power consumption for the invention to be reduced from approximately 5 Watts (W) to 1.25 W.

FIG. 1 is a perspective view of gas measuring system 100 coupled to host system 70 and configured to be removably secured to airway adapter 40, which is assembled with the components of a patient breathing circuit 20. Airway adapter 40 is typically assembled in breathing circuit 20 between an elbow 25, which is a connection to a patient interface, such as a mask or endotracheal tube, and "Y" piece 30 which is connected to a positive pressure generator such as a ventilator. Host system 70 provides the power to gas measurement system 100, receives the gas concentration signal, and derived measurements outputted from the gas measurement system, and in the case where the gas concentration signal is the carbon dioxide concentration signal, displays measurements such as: (a) the concentration of carbon dioxide in a patient's exhalations, (b) inspired carbon dioxide, (c) respiration rate, and (d) end tidal carbon dioxide. Similarly, where the gas concentration signal is the oxygen concentration signal, host system 70 displays measurements such as: (a) the concentration of oxygen in a patient's exhalations, (b) inspired oxygen, (c) respiration rate, and (d) end tidal oxygen.

As noted above, cable 120 communicates gas measurement system assembly 100 with host system 70. A distal end 110 of cable 120 is securely and removeably connected to the host system. A proximal end 123 of cable 120 includes a strain relief element 130 that permits tension to be applied to cable 120 without affecting the conductor within. Power is provided to the gas measurement system from the host through the cable. However, the present invention also contemplates that the gas measurement system may be battery powered with either an integrated or separate battery pack and communicate its data wirelessly to the host system, thereby eliminating the need for cable 120. Wireless communications using protocols known in the art, such as Bluetooth, Zigbee, UWB used in body area networks (BAN) and personal area networks (PAN) are contemplated. The gas measurement system may also be connected via a cable to a hub, which integrates the signals from gas measurement systems with other physiological measurement.

The end sections of airway adapter 40 (FIGS. 1 and 3) are designed for connection to patient interfaces and breathing systems. For example, the airway adapter may be disposed between an endotracheal tube (not shown) inserted in a patient's trachea and the breathing circuit of a positive pressure generator or ventilator 75. Gas measurement system 100, in the exemplary embodiment, is used to measure the carbon dioxide and oxygen levels of a patient. The particular airway adapter 40 illustrated in FIGS. 1 and 3 is not, by itself, part of the present invention. As such, the present invention contemplates that the gas measurement system of the present invention can be used with any conventional airway adapter, including absorption or luminescence quenching adapters. An adapter that has been adapted to measure gases via both infrared absorption and luminescence quenching is disclosed in U.S. patent application Ser. No. 09/841,451 to Mace et al., U.S. Pub. No. 2002/0029003 ("the '451 application"), the contents of which are incorporated herein by reference. Airway adapter 40 is typically molded from poly-carbonate or a comparable polymer.

Figure 14:
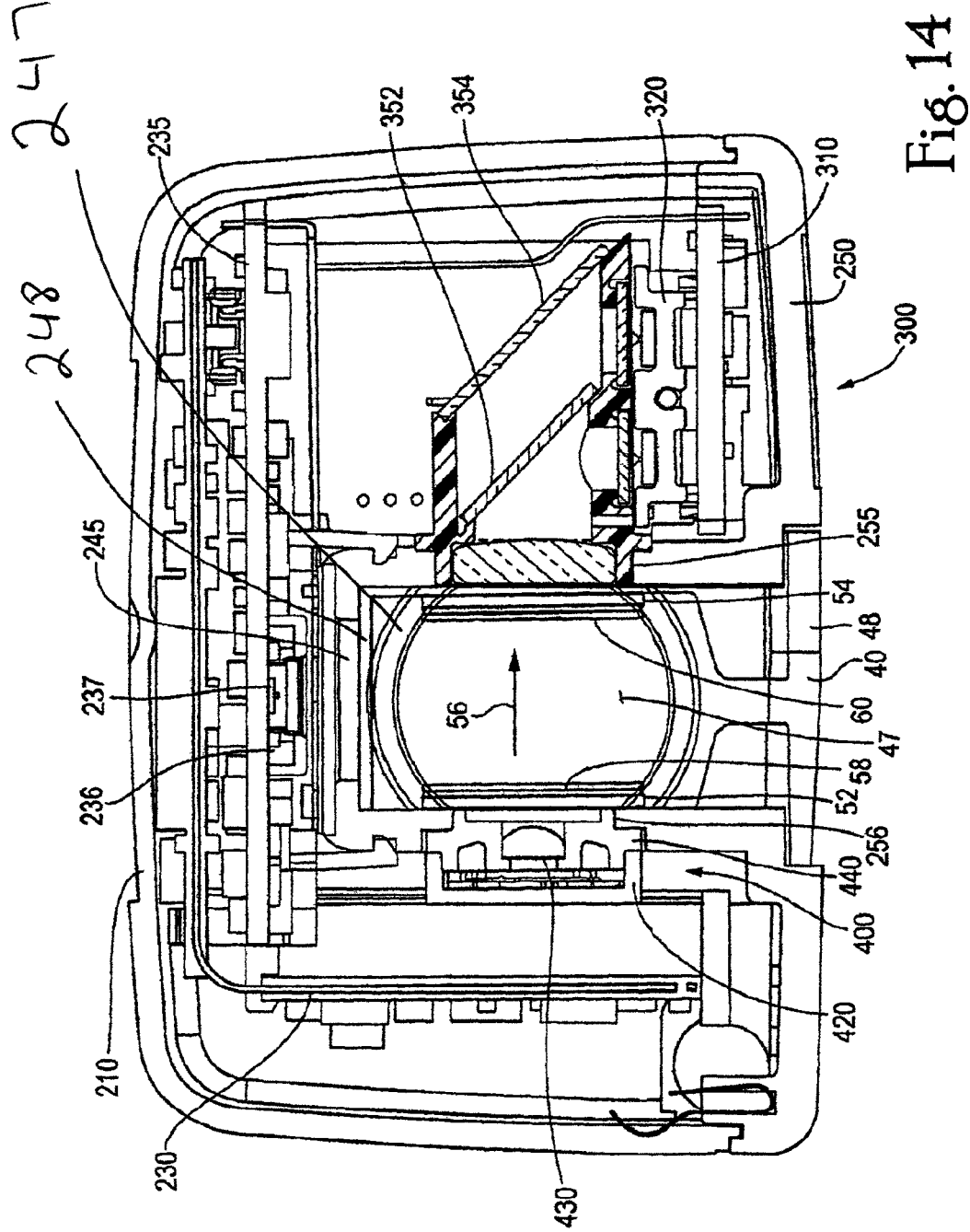
FIG. 14 is a cross-sectional perspective view of the assembled gas measurement system along line 14-14 of FIG. 4.

In an exemplary embodiment of the present invention shown in FIGS. 3 and 14, airway adapter 40 has a generally parallelepipedal center section 42 and two cylindrical end sections 44 and 46 with a sampling passage 47 extending from end-to-end through the adapter. End sections 44 and 46 are axially aligned with center section 42. Central section 42 provides a seat for gas measurement system 100. An integral, U-shaped casing element 48 positively locates gas measurement system 100 endwise on the adapter and, also, in that transverse direction indicated by arrow 50 in FIGS. 1 and 3. Arrow 50 also shows the direction in which airway adapter 40 is displaced to assemble it to gas measurement system 100. Apertures 52, 53, and 54 are formed in center section 42 of airway adapter 40.

With gas measurement system 100 assembled to the airway adapter, apertures 52 and 54 are aligned along an optical path 56 as shown, for example, in FIG. 14. Optical path 56 extends from a source assembly or emitter 400 in gas measurement system 100 transversely across airway adapter 40 and through the gas or gases flowing through the airway adapter. The optical path continues from the airway adapter to a detector assembly 300 in gas measurement system 100. To keep the gases flowing through airway adapter 40 from escaping through apertures 52 and 54 without unacceptably attenuating the infrared radiation traversing optical path 56, and to keep foreign material from the interior of the airway adapter, these apertures are typically sealed by infrared radiation transmitting windows 58 and 60. Additionally, aperture 53 is covered by a window 49. In physical communication with window 49 and located within the interior of airway adapter 40 is a sensing film with a photosensitive chemical. This chemical emits radiation in response to an excitation when the chemical is exposed to a gas, such as oxygen. It should be understood that the airway adapter can include one or more of apertures 52, 53, and 54, along with one or more of the gas measurement techniques that use these apertures.

Figure 4:
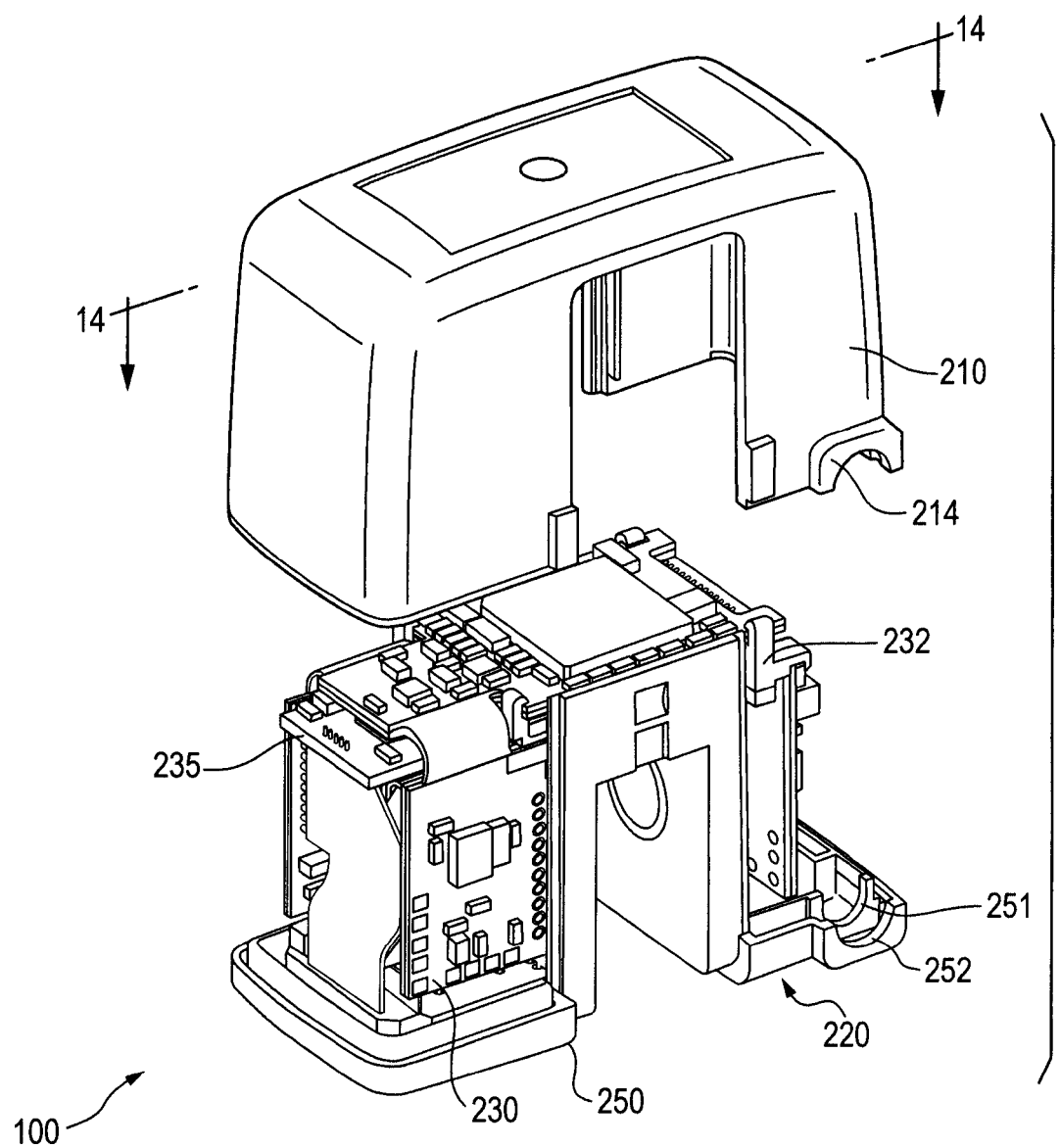
FIG. 4 is an exploded view of a gas measurement system with a cover and gas measurement system electro-optical assembly shown.

FIG. 4 is an exploded view of gas measurement system 100, which includes a polymeric cover 210 and a gas measurement system electro-optical assembly 220. Gas measurement system electro-optical assembly 220, which is perhaps best shown in FIGS. 4 and 7, includes the following components: (a) an infrared radiation source assembly 400 (shown in greater detail in FIGS. 12-13), (b) an infrared radiation detector assembly 300 (shown in greater detail in FIGS. 8-11), and (c) an optional luminescence quenching measurement circuit board 235. In the assembled gas measurement system, strain relief 130 is held in place by walls 214 and 252 provided on a base 250 and cover 210. Wall 214 which mates with wall 252 when the cover is attached to the base, which is accomplished using any conventional technique, such as a snap-fit or friction lock configuration.

Figure 5:
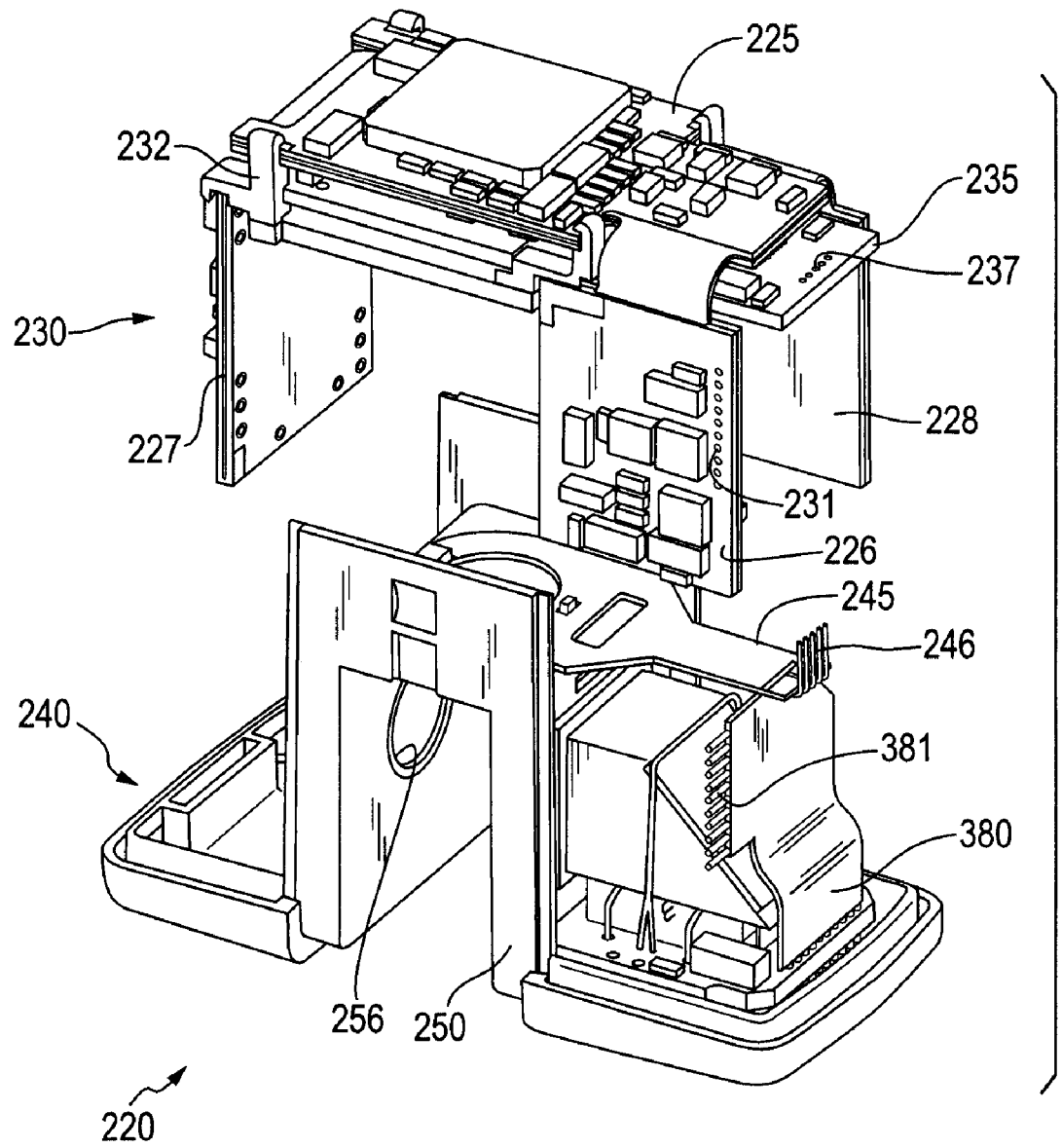
FIG. 5 is an exploded view of a gas measurement system electro-optical assembly.
Figure 6:
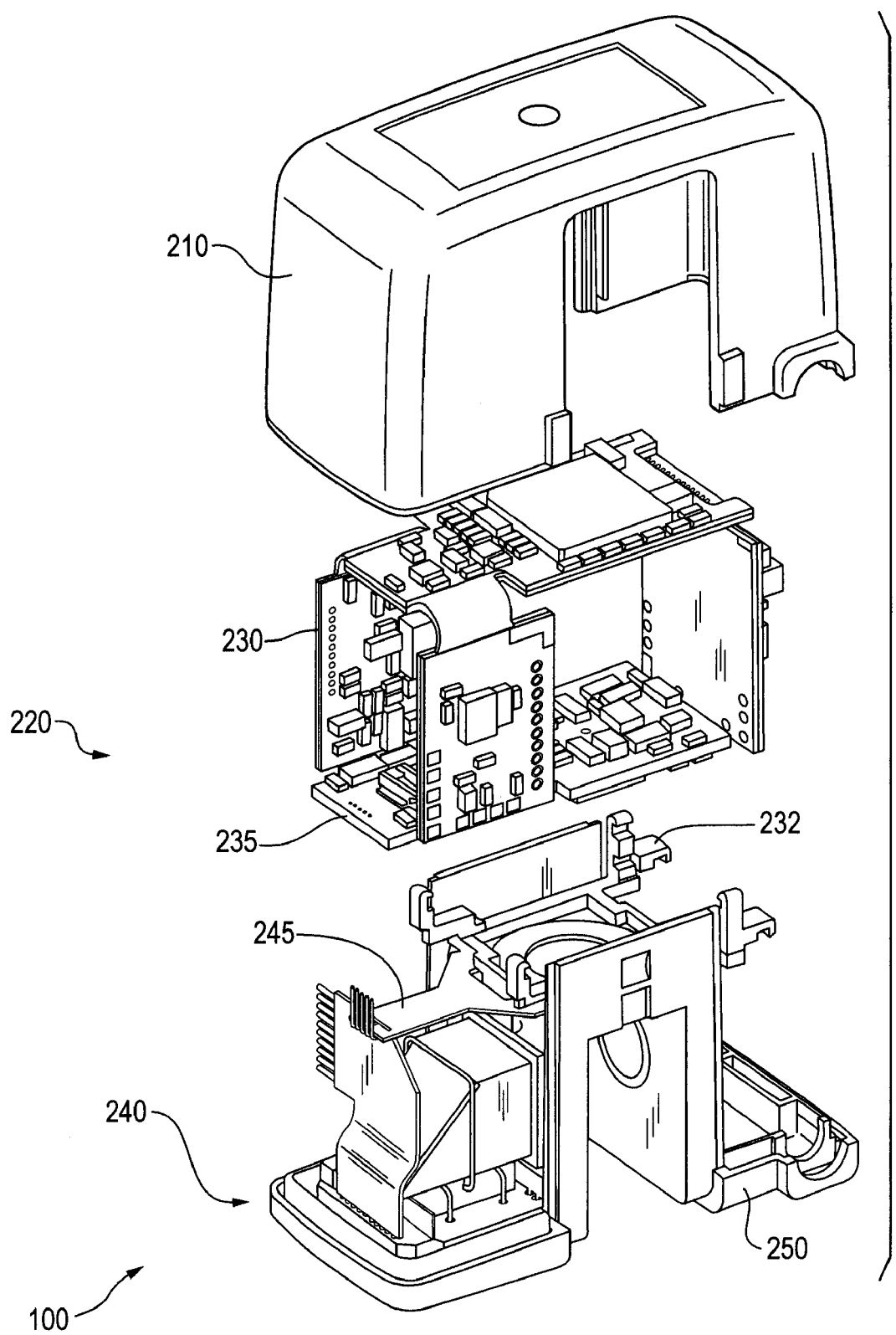
FIG. 6 is an exploded view of a gas measurement system with the cover, electronic circuit boards, and gas measurement system optical assembly shown.

Gas measurement system electro-optical assembly 220 shown in FIGS. 5-6 assembled with a flex circuit 230, a bracket 232, a luminescence quenching measurement circuit board 235, and an optical assembly, generally indicated at 240, which includes the optical elements for the gas measurement system. The source and detector assemblies in optical assembly are coupled to "U" shaped base 250 and mechanically and electrically connected to the flex circuit board, which is folded around these assemblies and attached to base 250. This assembly allows the performance of the gas measurement system's active components to be tested as a unit rather than individually before assembly. As a consequence, it is not necessary to wait until a gas measurement system is completely assembled to determine whether it will meet performance specifications. The result is significant cost savings, an objective that is furthered by the reduction of wiring and a significant reduction in the expense of assembly.

FIG. 5 is an exploded view of gas measurement system electro-optical assembly 220 with flex circuit 230, bracket 232, and luminescence quenching measurement circuit board 235 separated from gas measurement system optical assembly 240. Flex circuit 230 comprises rigid board portions 225, 226, 227, and 228 (see FIG. 15). The rigid portions are joined to each other by flexible portions. The flex circuit board includes the analog and digital circuitry required to drive the infrared source and to convert the signals from the detector assembly into an output values for infrared absorbing gases, such as carbon dioxide, and/or to convert the signals from the luminescence quenching assembly into output values for gases, such as oxygen. Circuit board 235 includes the circuitry and optical components for the measurement of oxygen via luminescence quenching techniques. Optical assembly 240 includes detector assembly 300, source assembly 400, and heater flex circuit 245 for controlling the temperature of the oxygen film. Heater flex circuit 245 is assembled with gas measurement optical assembly 240 at top of "U" shaped base 250. Pins 246 at distal end of heater flex circuit 245 are inserted into corresponding holes 237 in end portions of luminescence quenching measurement circuit board 235 prior to soldering. Similarly, pins 381 of detector flex jumper 380 are inserted into corresponding holes 231 along an edge of board portion 226 of flex circuit 230.

FIG. 6 is an exploded view of gas measurement system 100 showing the cover, the electronic circuit boards, and the gas measurement system optical assembly. Gas measurement system electro-optical assembly 220 with flex circuit 230, bracket 232, and circuit board 235 are shown separated from gas measurement system optical assembly 240.

Figure 7:
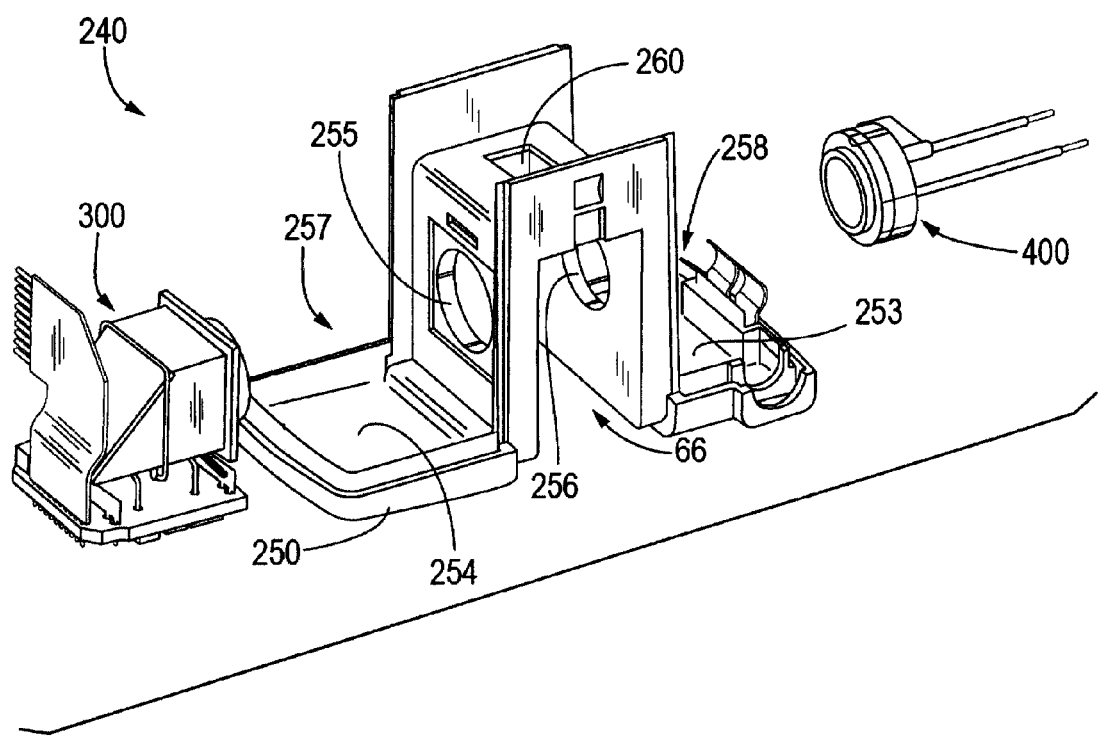
FIG. 7 is an exploded view of the gas measurement system optical assembly with the structural base member, detector assembly, and source assembly shown.

FIG. 7 is an exploded view of gas measurement system optical assembly 240 showing structural base member 250, detector assembly 300, and source assembly 400. Base member 250 of gas measurement system 100 supports source assembly 400 in a source assembly compartment 253 and supports and detector assembly 300 in a detector assembly compartment 254. A generally rectangular gap 66 is disposed between compartments 253 and 254. Gap 66 is configured to engage central section 42 of airway adapter 40. Defined in large part by the side walls and rims of base member 250, two pairs of complementary cavities in a first end section 258 and a second end section 257 cooperate to define infrared radiation source compartment 253 and infrared radiation detector compartment 254, respectively. Gas measurement system base member 250 may be molded from a polycarbonate or any other appropriate polymer. In the illustrated exemplary embodiment, base member 250 has a flat side wall and an integral rim oriented at right angles to the side wall.

A source aperture 256 is defined in a wall of the housing to provide an optical path for the radiation produced by the source assembly 400 to enter the sample cell portion of the airway adapter. A detector aperture 255 is defined in a wall of the housing to provide an optical path for the radiation passing exiting the airway adapter to reach detector assembly 300. In the illustrated embodiment, a luminescence quenching aperture 260, which corresponds to aperture 53, is also provided in the housing to measure the luminescence of the material quenched by the oxygen in the sample gas. It is to be understood that the luminescence quenching feature of the present invention and the absorption feature of the present invention can be used alone or in combination. Thus, depending on whether one or both of these gas measuring techniques are used, apertures 255, 256, and 260 can be eliminated.

Figure 8:
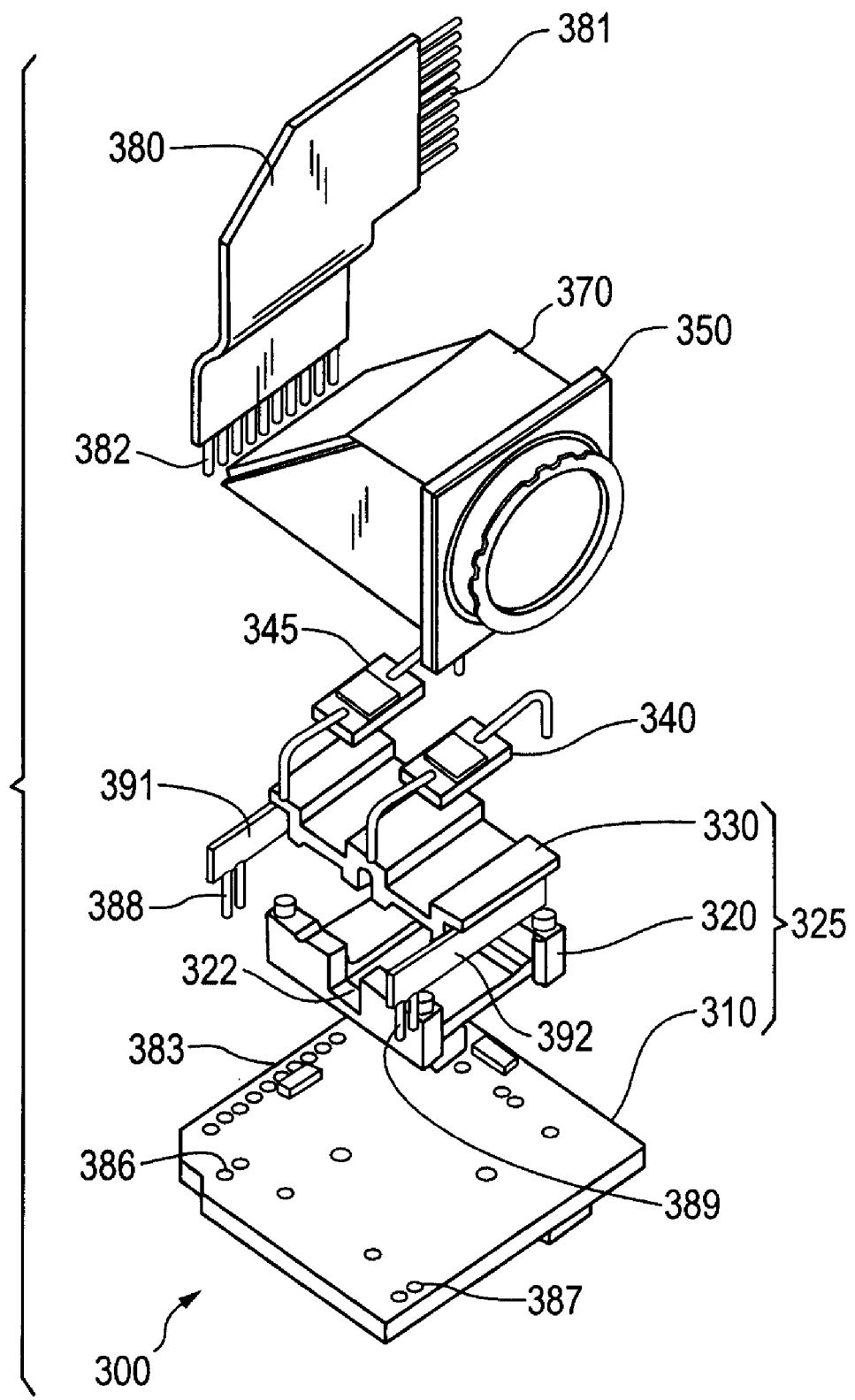
FIG. 8 is an exploded view of the detector assembly.
Figure 9:
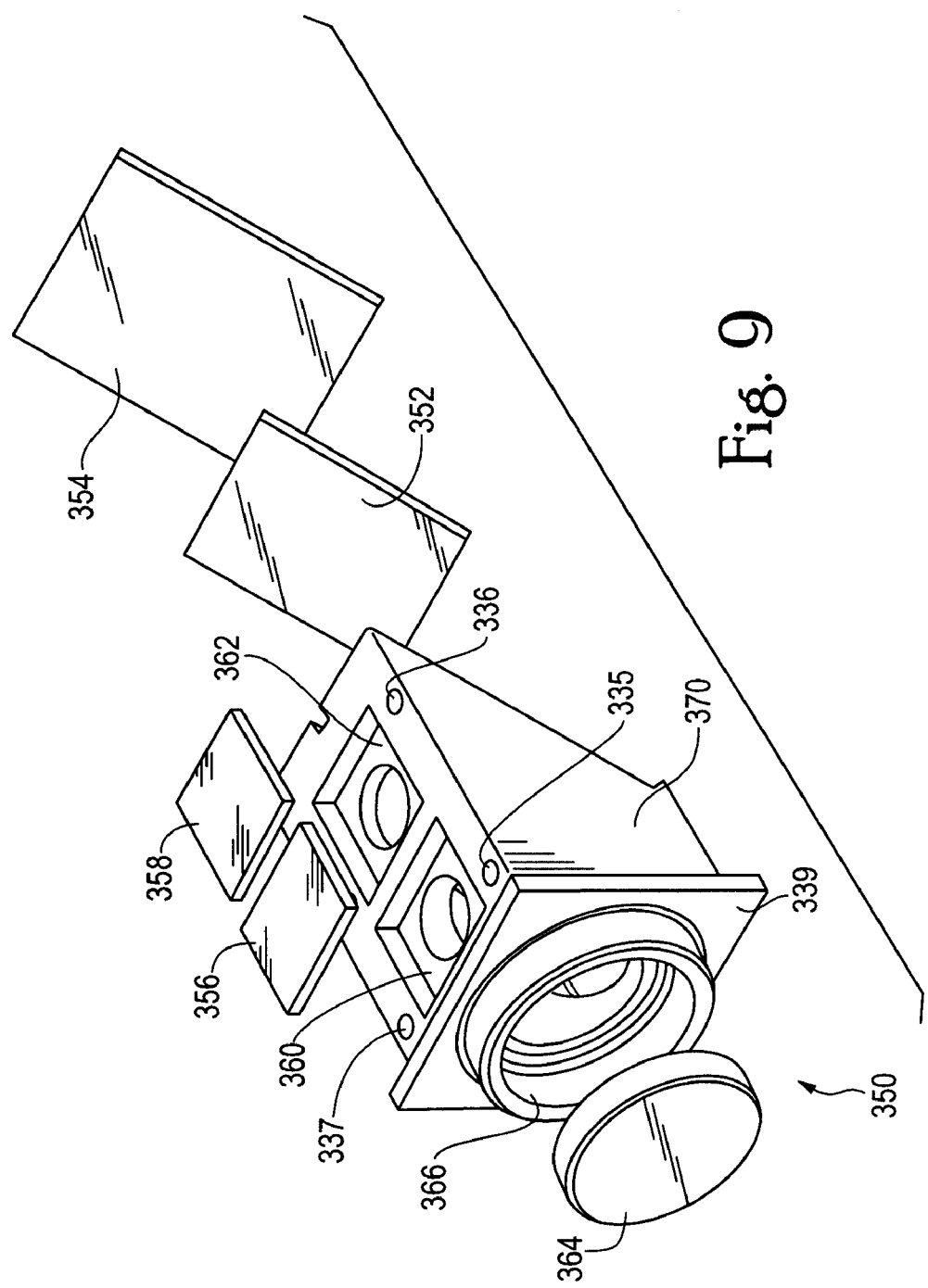
FIGS. 9 and 10 are exploded views of the optical housing assembly portion of the detector assembly.

FIG. 8 is an exploded view of detector assembly 300 of gas measurement system 100 and FIG. 9 is an exploded view of a detector optical assembly 350. Detector assembly 300 includes detectors 340 and 345 mounted on a heat sink 330, a heat sink spacer 320, and a detector assembly circuit board 310. Heat sink 330 is coupled to heat sink spacer 320, which is attached to a detector assembly circuit board 310. The resulting support assembly 325 is assembled to detector optical assembly 350 by aligning holes 335, 336, and 337 in an optical block 370 with corresponding locator pins on heat sink 330. Detector optical assembly 350 includes optical components, such as lens 364, filters 356 and 358, mirror 354, and beam splitter 352, and is assembled with detector support assembly 325.

Mounted in a recesses of heat sink 330 are data and reference detectors 340 and 345, which are aligned in the same plane (i.e., co-planar), thereby permitting more effective temperature regulation of the detectors. These detectors are preferably fabricated with lead selenide detector elements, because of the sensitivity which that material possesses to infrared radiation having wavelengths, which are apt to be of interest. Additionally, lead selenide data and reference detectors 340 and 345 are extremely temperature sensitive. It is, therefore, critical that these two detectors be maintained at the same temperature, preferably within the tolerance of not more that 0.02° C. Detectors 340 and 345 are maintained at the selected operating temperature by a detector heating system that includes detector heating elements 391 and 392, a temperature monitoring thermistor (not shown), and an operating/control circuit (not shown), which is located in the detector assembly circuit board 310 and flex circuit 230.

Detectors 340 and 345 are connected to detector assembly circuit board 310 to which a biasing voltage is applied across the identically configured and dimensioned infrared radiation sensing elements portions of the detectors. Gaps between the detectors and the boundaries of the detector-receiving recesses in isothermal support serve to electrically isolate the detectors from the conductive, isothermal support. A thermistor (not shown) is positioned so as to be centrally located in a groove 322 of heat sink spacer 320. Heating elements 391 and 392 are located at the ends of heat sink 330 and are in intimate contact with the heat sink. Heating element 391 and 392 include a flex circuit portion having a distally located surface mount resistor for delivery of heat.

Two pins 388 and 389 are provided in the heating elements to connect them to detector assembly circuit board 310. The flex circuit portion of heating elements 391 and 392 are placed in intimate contact with heat sink 330. In the exemplary embodiment, an epoxy, preferably with a high thermal conductivity, is employed to adhere the flex circuit portion of each of the heating elements to heat sink 330. Pins 388 and 389 of heating elements 391 and 392 insert into corresponding holes 386 and 387 on detector assembly circuit board 310. A detector flex jumper 380 interfaces detector assembly circuit board 310 to board portion 226 of flex circuit 230. Pins 382 of detector flex jumper 380 insert into corresponding holes 383 along an edge of detector assembly circuit board 310. Pins 381 of detector flex jumper 380 inserted into holes 231 of board portion of flex circuit 230.

Figure 10:
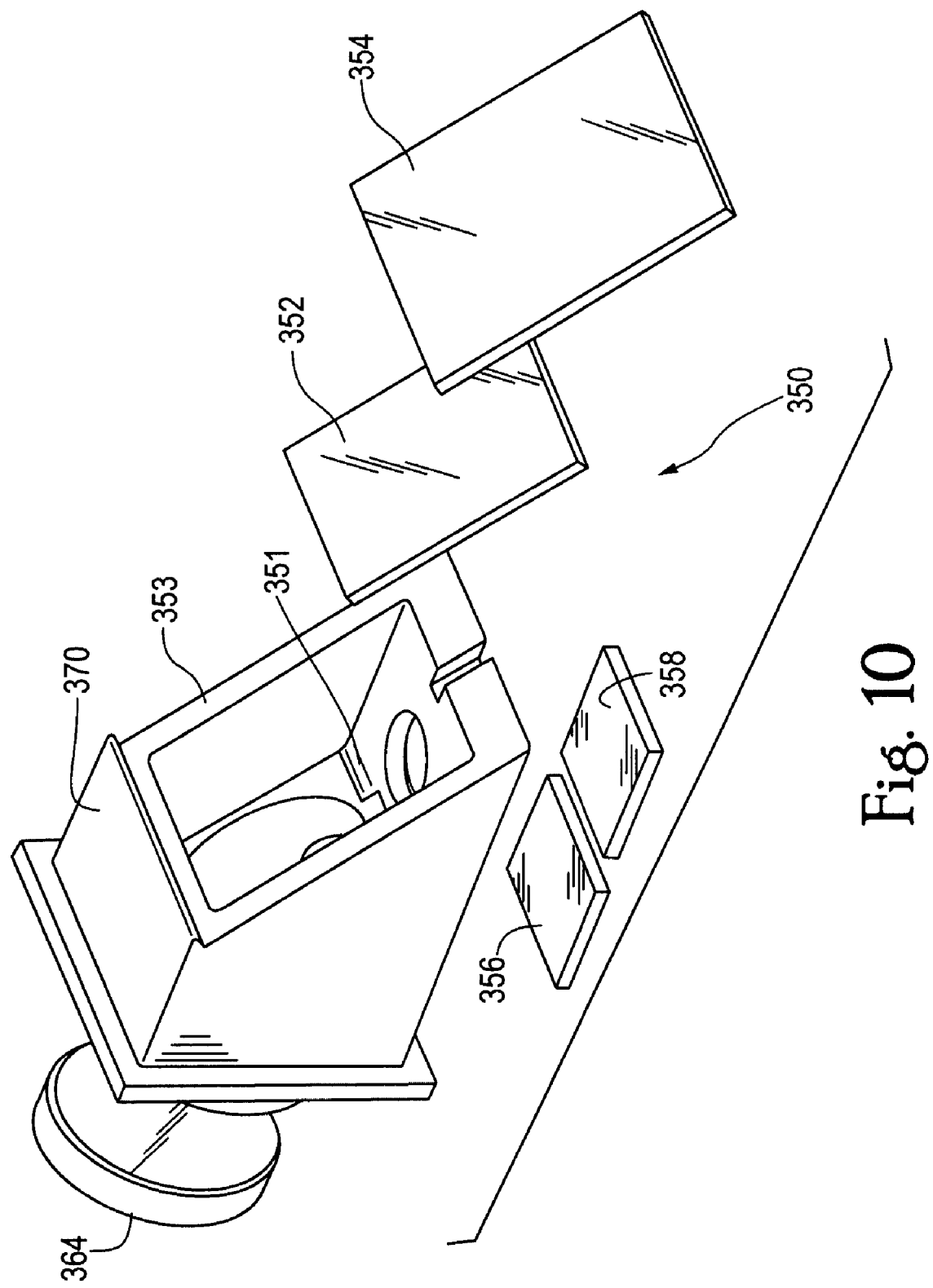
Figure 11:
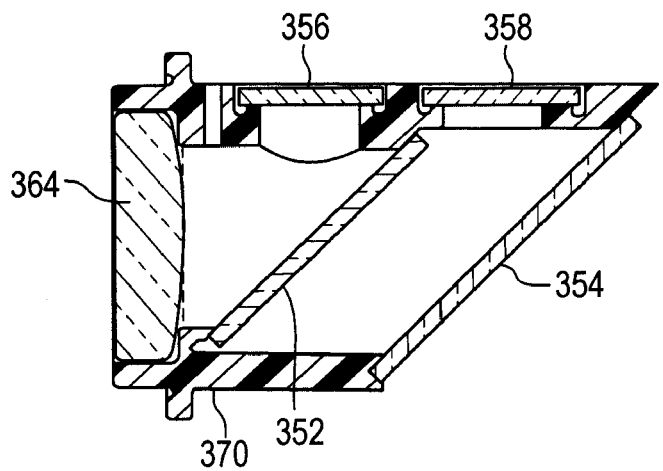
FIG. 11 is a cross-sectional view of the assembled optical housing assembly.

Detector optical assembly 350 will be described with reference to FIGS. 9-11. Detector optical assembly 350 includes beam splitter 352, mirror 354, filters 356 and 358, and detector lens 364. The beam splitter has a generally parallelepipedal configuration. This component is fabricated from a material such as silicon or sapphire, which is essentially transparent to electromagnetic energy in wavelengths of interest. The exposed front surface of the beam splitter is completely covered with a coating capable of reflecting that electromagnetic energy impinging on the beam splitter which has a wavelength longer than a selected value. In the illustrated exemplary embodiment of the invention, the coating will reflect to data filter 356 and data detector 340 energy having a wavelength longer than about 4 microns. The energy of shorter wavelengths is, instead, transmitted through beam splitter 352 to mirror 354 and to reference filter 358 and reference detector 272.

Beam splitter 352 is fixed in place by epoxying or otherwise bonding the beam splitter to ledge 351 which is integral to optical block 370. This accurately positions beam splitter 352 within optical block 370 with the advantage that subsequent adjustment of the beam splitter orientation is not required. Similarly, mirror 354 is fixed in placed by epoxying or otherwise bonding the mirror to ledge 353, which is also integral to optical block 370. Also, the electro-optical assembly of the present invention has an optimized focal length, which makes it possible to employ a smaller, less expensive detector assembly of the gas measurement system.

Bandpass filters 356 and 358 limit the infrared radiation energy respectively reflected from and transmitted by beam splitter 352 and impinging upon data and reference detectors 340 and 345 to energy in selected bandwidths. In the exemplary embodiment and use of the invention under discussion and depicted in the drawing, reference detector filter 358 is nominally centered on a wavelength of 3.7 microns. Such a filter transmits maximum energy near the carbon dioxide band absorbed by data detector 340. This absorption of maximum energy in an adjacent bandwidth is selected so that the output from reference detector 345 will be at least as large as the output from data detector 340. This contributes markedly to the accuracy of the gas concentration indicative signal subsequently obtained by ratioing the data and reference signals.

Data detector bandpass filter 356 is nominally centered on a wavelength of 4.26 microns. The carbon dioxide absorption curve is fairly narrow and strong, and bandpass filter 356 centers the transmission band within that absorption curve. Therefore, if there is a change in carbon dioxide level in the gas(es) being analyzed, the maximum modulation for a given change in carbon dioxide level is obtained. Data and reference bandpass filters 356 and 358 are bonded in recesses 360 and 362 of optical block 370. When optical block 370 is attached to the detector circuit board, data and reference bandpass filters 356 and 358 are aligned with data and reference detectors 340 and 345, respectively.

All of the energy over the entire and same span of infrared radiation beam propagated along optical path 56 and reaching detector assembly 300 with a wavelength longer than the selected cutoff is reflected to data detector 340. Similarly, energy with a shorter wavelength is transmitted through beam splitter 286 to reference detector 345. Because of this, the physical relationship of detectors 340 and 345 discussed above, and the dimensioning and configuration of the energy intercepting sensing elements of those detectors, both detectors "see" the same image of the beam of electromagnetic energy. This contributes markedly to the accuracy afforded by detector assembly 300.

In other words, and optically, with the data and reference detectors 340 and 345 accurately positioned relative to each other, and beam splitter 352 situated in the manner described above, these components function as if the two detectors were precisely stacked one on top of the other. Therefore, electromagnetic energy from the beam reaches both detectors in spatially identical fashion. By making the two detectors 340 and 345 spatially coincident from an optical viewpoint and electronically sampling the detector outputs at the same times, the adverse effects on accuracy attributable to foreign material collecting on either of the above-described airway adapter optical windows 58 and 60, the window 460 of source assembly, or a subsequently described window 364 of detector assembly 300 are also effectively eliminated by the subsequent ratioing of the data and reference detector output signals.

The electromagnetic energy in the beam propagated along optical path 56 reaches beam splitter 352 through an aperture 366 defined in a front wall 339 of optical block 370. An infrared radiation transparent lens 364, typically made of sapphire, spans aperture 366 and keeps carbon dioxide and other foreign material from penetrating to the interior of optical block 370. Lens 364 is bonded to the optical block in any convenient and appropriate manner.

Infrared radiation source assembly 400 will now be described with reference to FIGS. 12 and 13. Infrared radiation source assembly 400 emits infrared radiation in the form of a beam 480 (see FIGS. 14 and 16), which propagates along optical path 56. The infrared radiation source assembly includes an infrared radiation emitter 445, commutators/lead frames 446 and 447 disposed in a source ring assembly 420, and a lens 460 mounted in a lens holder 440 attached to source ring assembly 420. Infrared radiation emitter 445 includes a substrate formed from a material having low thermal conductivity. This is significant because it dramatically reduces the power required to heat the emitter to the operating temperature. When current is applied across a emissive layer 448 of emitter 445, heating up the emissive layer and substrate, the substrate grows or increases in length due to thermal expansion, but this growth is accommodated by an elastic bonding agent rather than being constrained. As a consequence, the stresses, which would be imposed upon emitter if both ends were rigidly fixed, are avoided, eliminating the damage to emitter or complete failure of that component which might result if high mechanical stresses were imposed upon it.

Emitter 445 of source assembly 400 is energized to heat it to an operating temperature in which it emits infrared radiation in an appropriate range of bandwidths by effecting a flow of electrical current through emissive layer 448 from an appropriate power supply. The power supply is connected to emissive layer 448 via electrical leads 451 and 452. These leads are soldered or otherwise physically and electrically connected to at opposite ends of commutators 446 and 447.

Commutators 446 and 447 are installed in source ring 420 of source assembly 400. The environment in which this component operates can reach an elevated temperature due to heating by emissive layer 448 of infrared radiation emitter 445. The source ring is, therefore, fabricated of a polymer that remains structurally stable at the temperatures it reaches during the operation of infrared radiation emitter 445. In the illustrated exemplary embodiment, source ring 420 has a cylindrical configuration with an integral wall 454 and base 453. Projecting in the same direction from base 453 are assembly locating bosses or lugs 456, 457, 458, and 459. Spaced apart lugs 456 and 457 and the complementary, spaced apart lugs 458 and 459 embrace the opposite sides of commutators 446 and 447. Bosses or lugs 461 and 462 separate the commutator segments, providing gaps therebetween to electrically isolate the two commutator segments. This is necessary so that a voltage differential can be created across emitter 445 to cause operating current to flow through the emitter.

Figure 12:
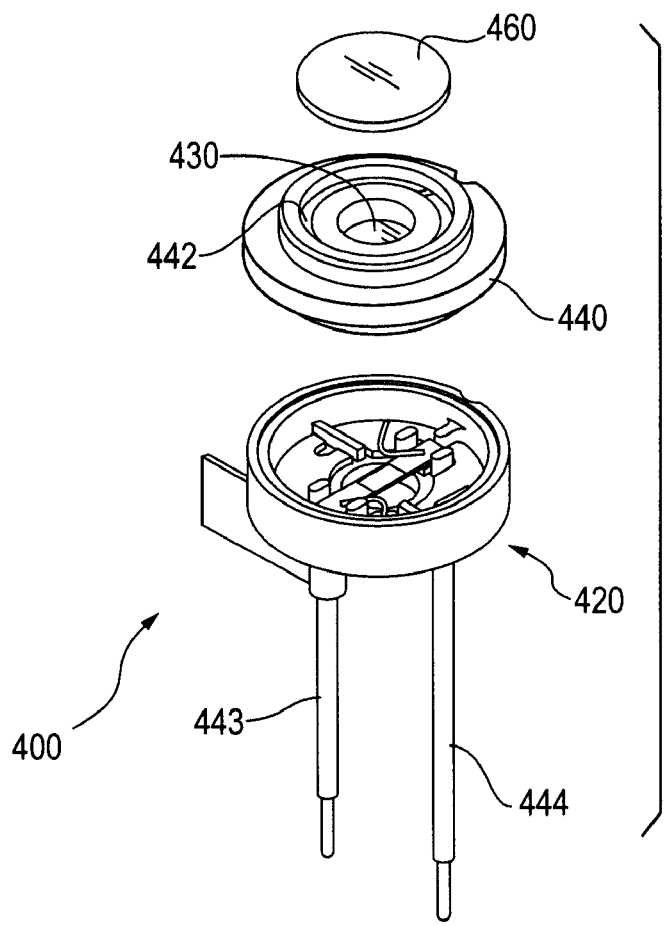
FIG. 12 is an exploded view of the source assembly.
Figure 13:
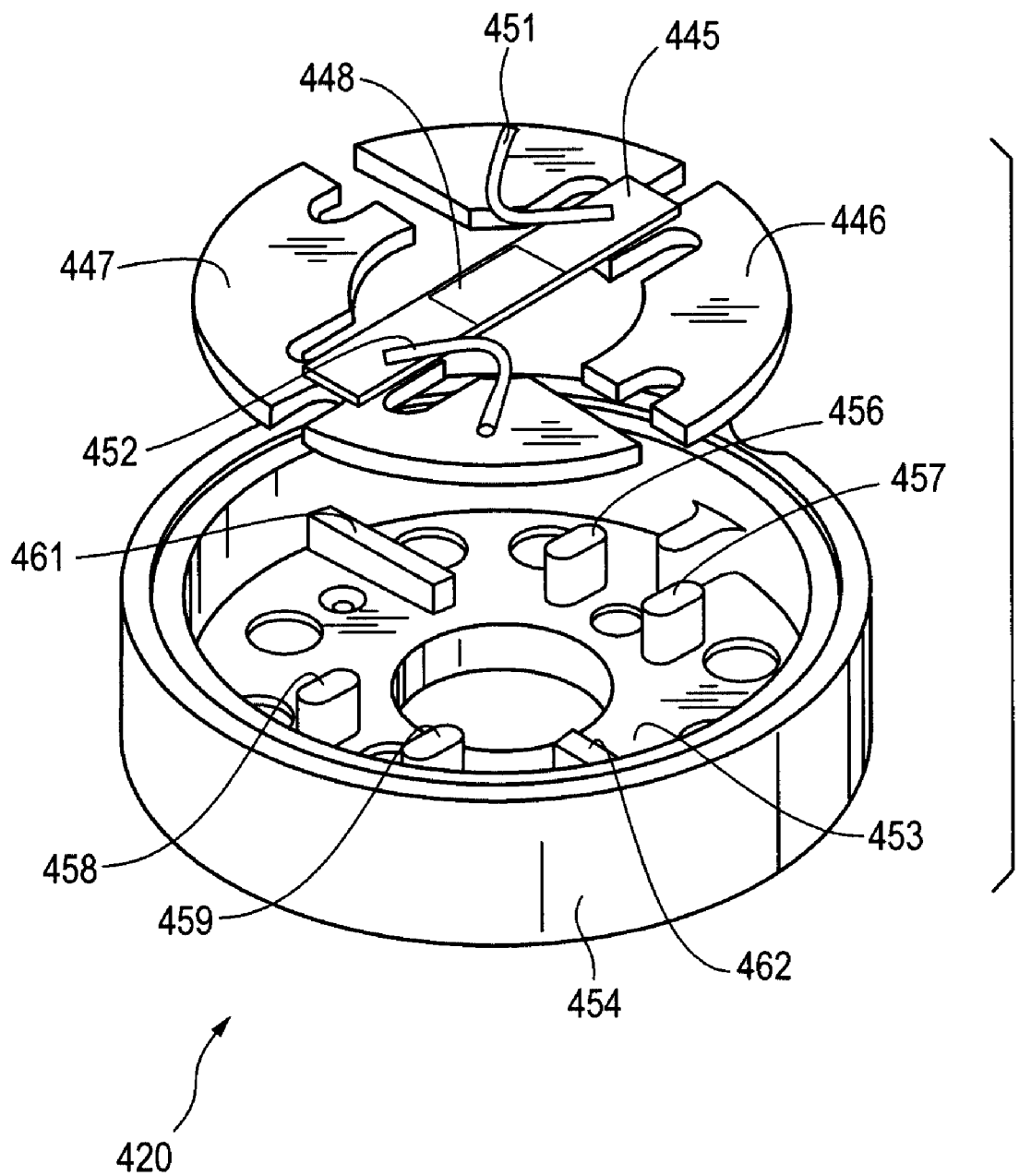
FIG. 13 is an exploded view of the emitter housing portion of the source assembly.
Figure 15:
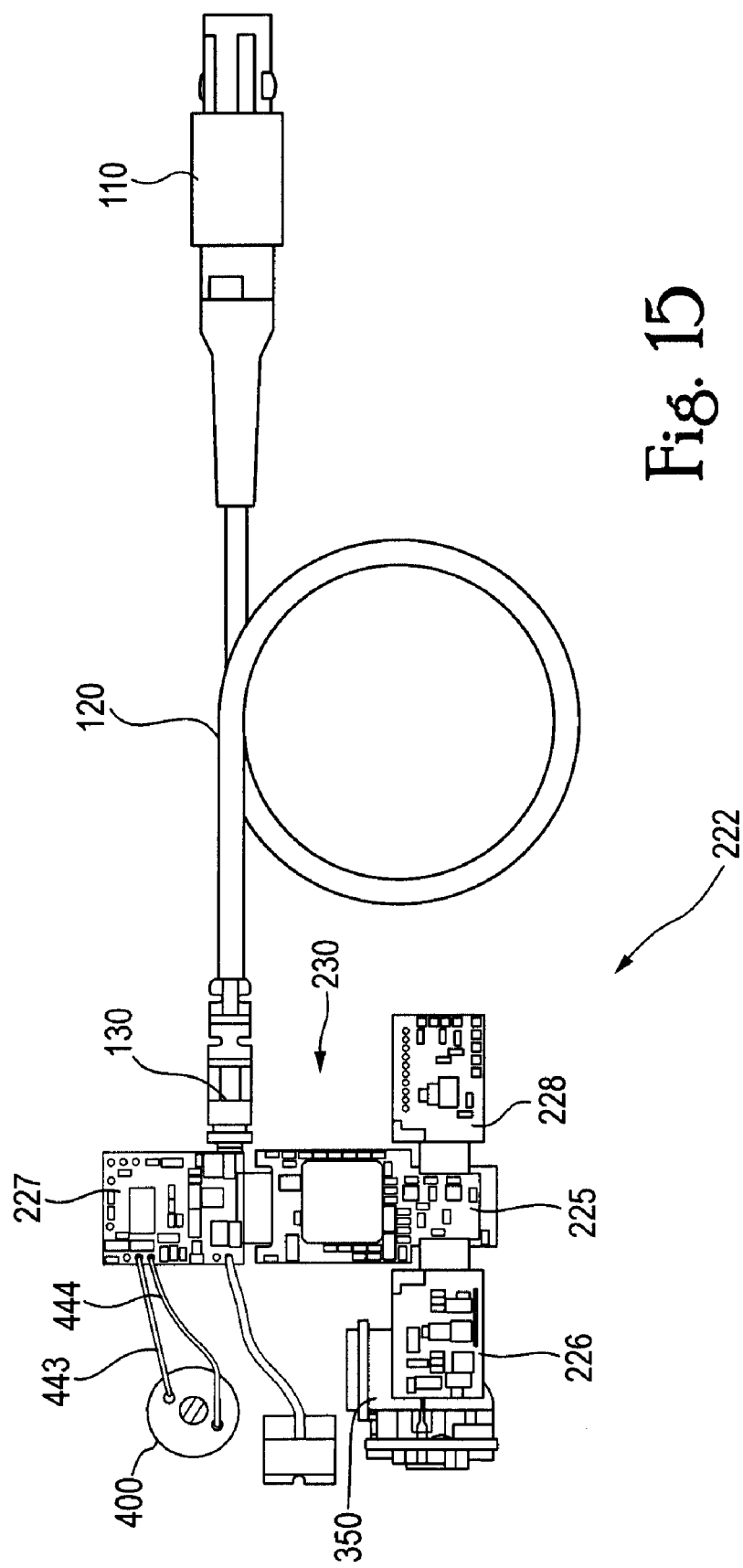
FIG. 15 is a flattened view of the assembled components of the gas measurement system prior to placement in the housing.
Figure 16:
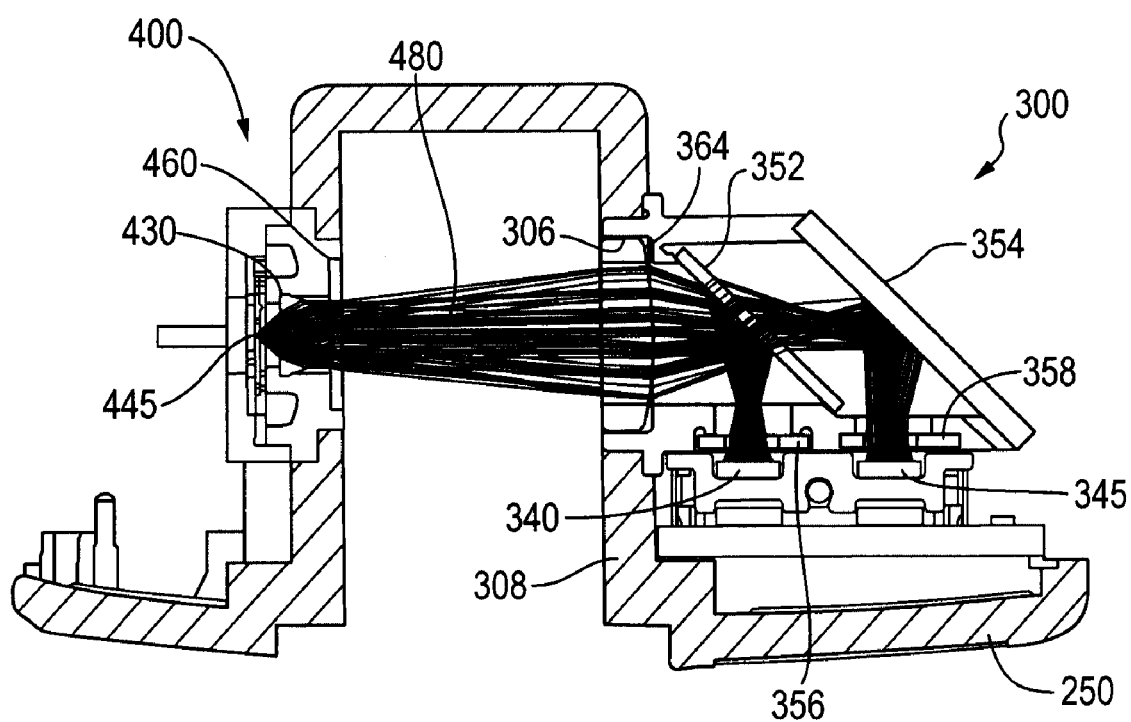
FIG. 16 is a ray tracing of the optical path within the gas measurement system according to the principles of the present invention.

Referring now to FIGS. 14-16, as well as FIGS. 12 and 13, infrared radiation outputted by emissive layer 448 of infrared radiation emitter 445 is focused and propagated along optical path 56 through a lens 430 disposed in a lens holder 440. Foreign material is kept from the interior of the infrared radiation source assembly 400 by a sapphire or other infrared radiation transmitting window 460 spanning and closing aperture in which lens 430 is mounted. Window 460 is cemented or otherwise bonded to a ledge or groove 442 formed in lens holder 440 of infrared radiation source assembly 400.

Energy in a specific band is absorbed by the gas of interest flowing through the airway adapter (typically carbon dioxide) to an extent proportional to the concentration of that gas. Thereafter, the attenuated beam of infrared radiation passes through the aperture 306 in the front wall 308 of the detector portion of housing 210, is intercepted by beam splitter 352, and is either reflected toward data detector 340 or transmitted to reference detector 345 after reflected by mirror 354. Bandpass filters 356 and 358 in front of those detectors limit the energy reaching them to specified (and different) bands. Each of the detectors 340 and 345 outputs an electrical signal proportional in magnitude to the intensity of the energy striking that detector. These signals are amplified by electronic circuitry on detector system circuit board 310 and conducted to a digital signal processor on board portion 225 of flex circuit 230. The processor typically ratios the signals from the detectors to generate a third signal accurately reflecting the concentration of the gas being monitored.

Optical path 56, the distance transversed by the infrared radiation between windows 58 and 60 mounted in apertures 52 and 54, respectively, and located within integral "U" shaped casing element 48 of airway adapter 40, is shown. The optical alignment features of base 250 are readily apparent from the cross-sectional view. Features of lens holder 440 attached to source ring assembly 420 serves to properly align source assembly 400 within base 250. Similarly, features of detector optical assembly 350 serves to properly align detector assembly 300 within base 250.

Luminescence quenching optical system 236 is assembled to luminescence quenching measurement circuit board 235. Luminescence quenching measurement circuit board 235 includes the circuitry to drive excitation source 243 and measure the response with detectors 238 and 239 using either amplitude or phase based detection techniques. The exemplary luminescence quenching optical system 236 includes excitation source 243 and detectors 238 and 239 positioned on each side of excitation source 243 (see FIG. 29).

FIG. 15 is a flattened view of the assembled components of the gas measurement system prior to placement in the housing. Prior to assembling detector assembly 300 and source assembly 400 to "U" shaped base 250, these assemblies are physically and electrically interfaced to flex circuit 230. Detector assembly 300 is connected to board portion 226 of flex circuit 230 with detector flex jumper 380 (FIGS. 5 and 8). The ends of leads 443 and 444 (FIG. 12) of source assembly 400, and the connectors in cable 120 are connected to board portion 227 of flex circuit 230. To assemble flattened electrooptical assembly 222 to base 250, source assembly 400 and detector assembly are attached to base 250. Board portion 225 of flex circuit 230 is placed at top of the "U" of base 250. Board portion 228 is folded to fit in detector assembly compartment 254 and board portion 227 is folded to fit in source assembly compartment 253.

FIG. 16 is a ray tracing of the optical path within the assembled gas measurement system. Rays 480 in FIG. 16 are illustrative only and shown as if emissive layer of emitter 445 is a point source. The infrared rays from emitter 445 are collimated by half-ball lens 430. The concave shape of airway side of the lens serves to "focus" the rays into a parallel. The rays impinge upon infrared absorptive gases and substances that are within the airway adapter and are absorbed and scattered. The remaining rays pass through the window of airway adapter and entered detector assembly 300. The rays pass through lens 364 and are collimated/focused onto beamsplitter 352, where approximately half of the rays are reflected and pass through filter 356 and detector 356, and the other half are transmitted and reflected by mirror 354 onto filter 358 and detector 358.

Figure 17:
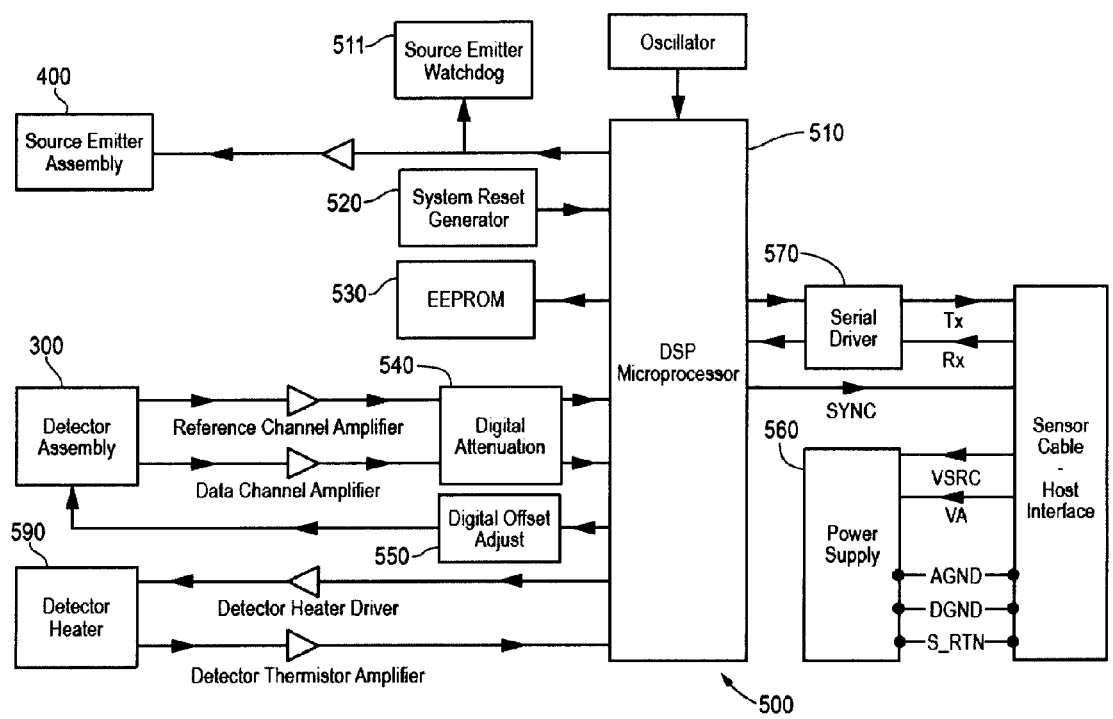
FIG. 17 is a block diagram of the gas measurement system according to the principles of the present invention.

FIG. 17 is a block diagram of the gas measurement system 500 according to the principles of the present invention. A microprocessor 510 provides the control, measurement, and signal processing functions of this invention. An exemplary processor is the TMS320F2812 DSP manufactured by Texas Instruments. Microprocessor 510 provides the source timing signals to source assembly 400, which is driven by a pulsed voltage of 5.0 V DC in a uni-polar fashion. A source emitter watchdog 511 monitors the source pulse width and maintains it within an allowable window. A system reset generator 520 is employed during the power up sequence, so that the processor will only reset once a stable voltage is reached and during the down sequences so that an orderly power down sequence will occur.

The executable program, which may stored in an EEPROM 530 or elsewhere, is communicated to microprocessor 510. Data and reference channel signals from detector assembly 300 are amplified by a digital attenuation 540 prior to analog to digital conversion within microprocessor 510. A detector heater 590 located within detector assembly 300 is controlled by a feedback loop by microprocessor 510. The low level signals from the detectors are AC coupled, amplified, and level shifted to allow for complete signal acquisition. Dual sample and hold stages within the ADC provide simultaneous sampling of the data and reference channels. Active gain and offset adjustment compensate for the optical and electronic variables in the signal chain. Detector heater driver controls the delivery of energy to detectors while detector thermistor driver provides the thermistor signal to the processor. A control algorithm such as a PID controller serves to regulate the temperature typically between 40° C. and 50° C. to within ±0.02° C. The detector heater is powered by the +5 V DC supply, which is also used to power the analog circuitry regulator. Window heater 245 includes a temperature sensing component as well as heating component. Electronics on circuit board 235, in conjunction with the microprocessor, control the delivery of energy to the heating component. A control algorithm within microprocessor 510 using the sensed temperature maintains the temperature of the heating element to a temperature sufficiently above ambient temperature within the airway adapter. CODEC 555 is a decoder and encoder with integrated digital-to-analog converters and analog-to-digital converters. CODEC 555, which interfaces with microprocessor 510, modulates excitation source 243 using the output of detectors 238 and 239 in such a manner to perform phase-based measurements of lifetime. Serial driver 570 communicates bi-directionally using a transmit and receive line denoted Tx and Rx respectively. Power supply 560 receives power from VSRS and VA lines with signal return and a digital and analog ground provided.

The above-described exemplary embodiment of the present invention has shown an optical assembly with a infrared detector system in a linear configuration that includes a single beamsplitter, single mirror, two filters, and two detectors. This configuration is well suited to measure a single gas flowing through the sample cell. However, there is an increasing need to measure additional gasses using a transducer that is the same size as that used to makes a single gas measurement. To this end, the present invention contemplates other embodiments for the gas measurement systems that includes an infrared spectrometer portion capable of measuring multiple gases. For example, a four channel system would permit quantification of the concentrations of carbon dioxide, nitrous oxide, and certain anesthetic agents, along with a reference channel. The present invention may also be adapted as an efficient non-dispersive infrared multi-channel gas analysis configuration that use one or more of the following novel features and combinations:

a) multiple dichroic beam splitters that divide the spectrum in a binary sequence, with narrow bandpass filters to select specific wavelengths;

b) combinations two or more dichroic splitters on a single substrate;

c) geometrical configurations in which all detectors are disposed on a single plane, and can use a single turning mirror for multiple channels;

d) a broadband bandpass filter in place of two dichroic splitters;

e) toroidal focusing mirrors, and in combination with sapphire or germanium lenses; and/or f) lenses on both sides of a beam splitting element to compactly provide independent control of reflected and transmitted light.

Figure 18:
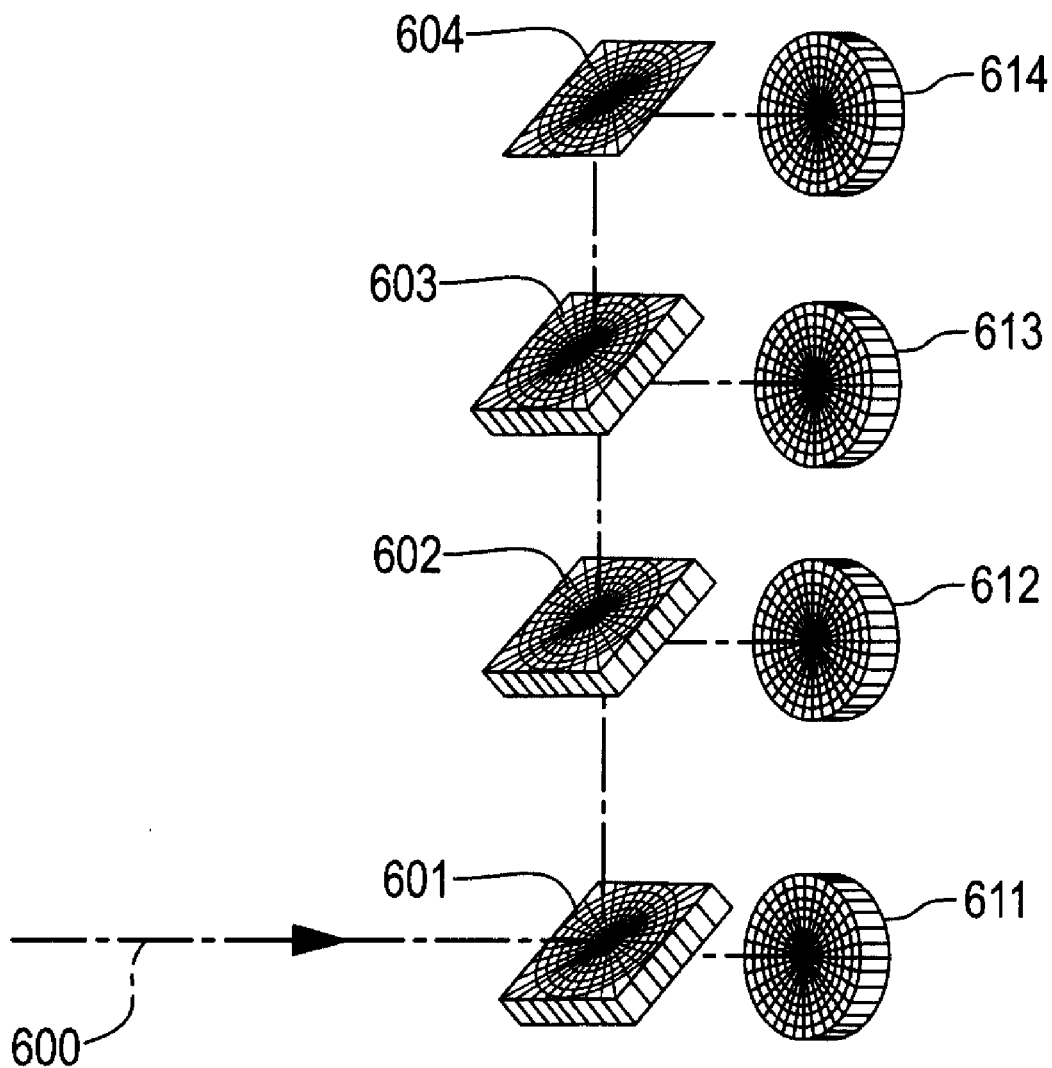
FIG. 18 is a schematic diagram of a four channel optical system in a plain linear configuration for the optical assembly of the detector assembly according to the principles of the present invention.

FIG. 18 is a schematic diagram of an exemplary embodiment of an optical system disposed in a linear configuration according to the principles of the present invention. The optical system in the this embodiment consisting of four channels, each having a narrow bandpass filter and detector. Each of the filter/detector assemblies 611, 612, 613, and 614 use similar detectors, but filters each with different passbands. The beam from the infrared source, after having passed through the sample cell, enters the optical system. This beam is indicated by reference numeral 600 in the figures. Beam 600 strikes a first dichroic beam splitter 601. First dichroic beam splitter 601 may be configured to pass either the shortest wavelength of interest or pass the longest wavelength of interest. All other wavelengths would be reflected. The other wavelengths, or channels, are split off from the reflected beam in sequence by second and third dichroic beam splitters 602 and 603. The sequence of the beam splitter wavelengths is somewhat arbitrary. The final element, plain mirror 604, reflects the final channel, to the detector or filter/detector assembly 614. The use of this mirror permits all detectors to be on the same plane (i.e., coplanar).

Figure 19:
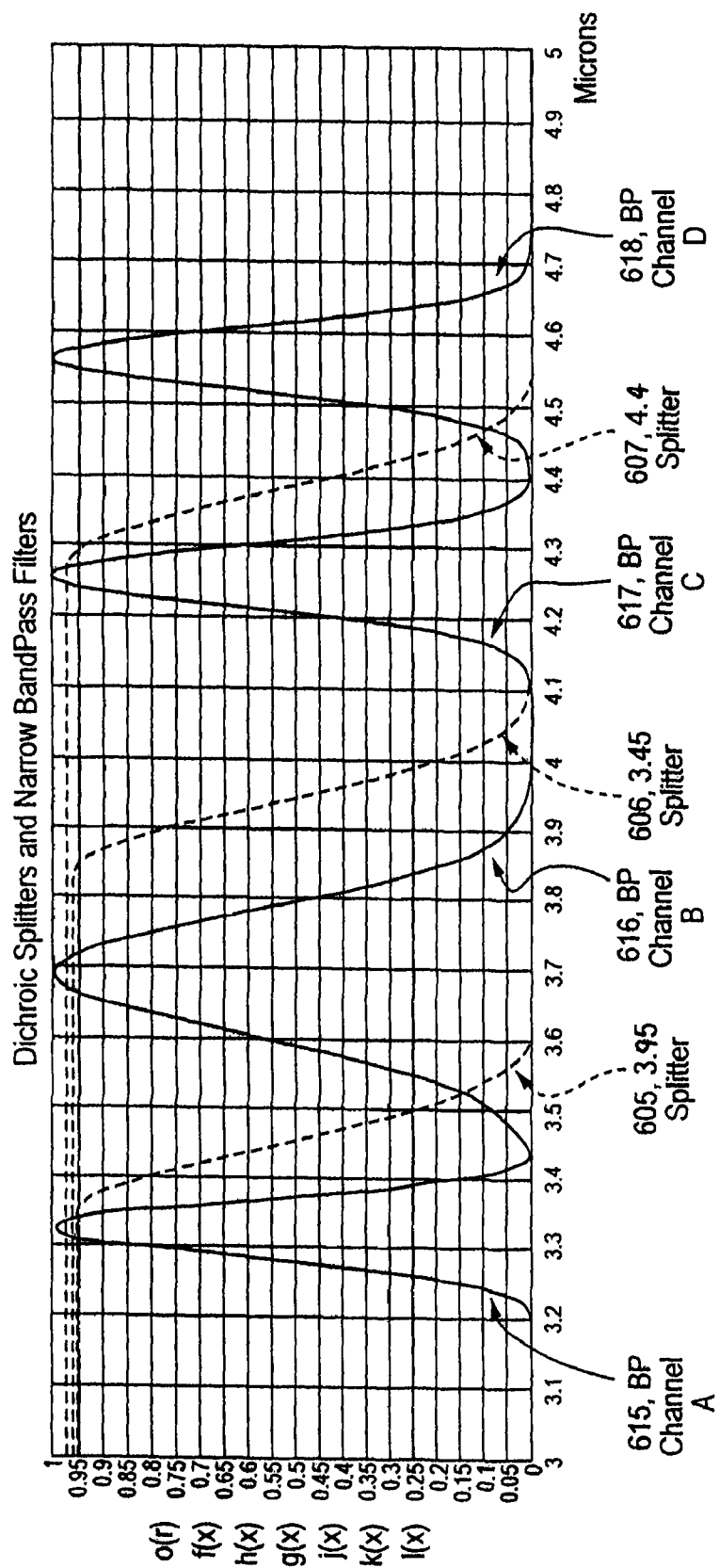
FIG. 19 is a chart showing one embodiment of the beam splitter wavelengths relative to the filter wavelengths.

FIG. 19 illustrates the filter characteristics of short (low) pass beam splitters 605, 606, and 607 as a function of wavelength relative to the filter characteristics of bandpass filters 615, 616, 617, and 618 for each of the channels in the linear system of FIG. 19. Each detector has a narrow band filter to select the required wavelength for detection with more specificity than may be done with dichroic beamsplitters. Note that the logic could be inverted, in the sense that the first beamsplitter could pass the longest wavelength, 618, and reflect the other wavelength to filters 615, 616, 617. Then the following beamsplitters could be short pass, in which case the sequence would be 617, 616, and 615, or they could be long pass, with a sequence 615, 616, and 617.

Alternatively, long and short pass could be mixed in certain sequences. Note that dichroic beam splitters are used instead of the more conventional broadband beam splitters in order to materially improve the amount of signal energy that will reach the detectors, especially the last detector. This linear system has the advantages of a simple design and all detectors are on the same plane. However, the beam spreads substantially along the path length to the final detector, so the energy collected by the last detector is less than previous detectors.

Figure 20:
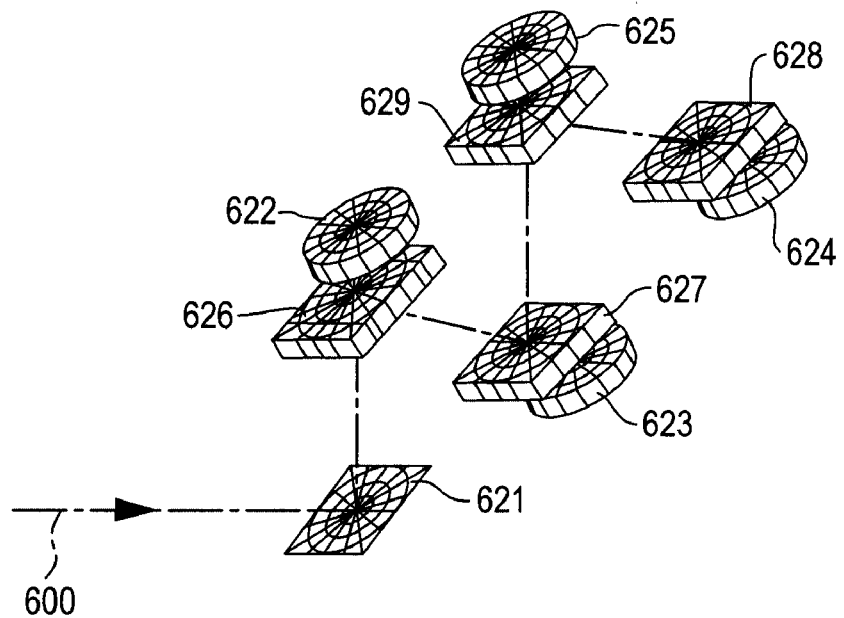
FIG. 20 is a schematic diagram of a four channel optical system in a zigzag configuration.

FIG. 20 is schematic diagram of an optical system having a zigzag configuration. This system makes use of the fact that a dielectric bandpass filter will reflect all wavelengths that are not transmitted. In effect, there is a conservation of energy. In the case of the zigzag, the first element is a mirror 621. Each of the beamsplitters 626, 627, 628, and 629 are narrow bandpass filters. Because all energy that is not selected for a particular channel is reflected on to other channels, the sequence of filter/detector assemblies 622, 623, 624, and 625 are arbitrary. Note that each filter must be designed to operate at the chosen angle (typically 40° to 45°). The system has a shorter path length, and a lower parts count, because the narrow bandpass filters perform a dual function of sequencing the channels, as well as narrowly defining the desired wavelength. The detectors are now on two planes, but the detector assemblies are identical. The system as drawn shows the light path from the source to final detector in the same plane. For ease in packaging, the assembly following the mirror 621, may be rotated 90 degrees about the optical axis, so that the source optical axis would be normal to the plane of the zigzag.

Figure 21:
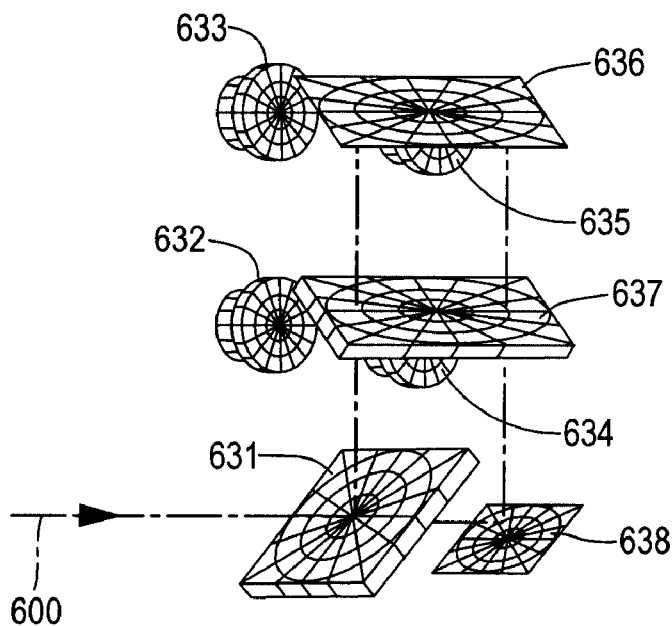
FIG. 21 is a schematic diagram of a four channel optical system in a square array configuration.

FIG. 21 is schematic diagram of an optical system having a square array configuration. Dichroic beam splitters are used in a more direct binary selection process. For example, using the characteristics of the filters and beamsplitters shown in FIG. 21, the first beamsplitter 631 may be set at 4 microns to divide the spectrum of interest in half. The reflected half is split again at 4.4 microns, with the reflected part going directly to the narrow bandpass filter/detector assembly 632, while the pass part is subsequently reflected at mirror 636 to narrow bandpass filter/detector assembly 633. The half that is passed by beamsplitter 631 is reflected at mirror 638, to beamsplitter 637, which is set at 3.45 microns. As in the first described leg, beamsplitter 637 splits and directs the beam to narrow bandpass filter/detector assemblies 634 and 635. The paths of the beam channels 1 and 2, and channels 3 and 4 have been rotated about the optical axis at mirror 636 and beamsplitter 631 respectively. By this device of "twisting the legs", all the detectors can be placed in close proximity on the same plane. Additionally, in this system, the two mirrors, shown as mirror 636, can be manufactured as a single piece, and the beamsplitters, shown as beamsplitter 634, can also be formed on a single substrate.

It should be noted that the combination beamsplitter can be built as a pair of overlapping dichroic beamsplitters, with one on each side of a sapphire substrate, or it could be built as a wide bandpass filter, where the band edges form the wavelength splitting function. The following described systems may appear somewhat similar in general architecture, but they contain focusing elements in the forms of sapphire lenses, concave spherical mirrors, or concave aspherical mirrors.

The system advantage to added focusing elements is a greatly improved energy collection efficiency at each detector. Without the focusing elements, the beam from the source will be much larger than the detectors at the detector plane. This oversize comes about for 2 reasons: system magnification, and aberrations. The ratio of the distance from the source mirror to the focal point to the distance from the source to the source mirror is the magnification. Depending on where the focus is set, the magnification will be in the range of 8 to 10. The source is about 0.02" in diameter, so an image at the detector plane will be in the range of 0.16" to 0.2". But the detectors are typically 0.08" diameter (larger detectors are possible, but the cost rises quickly with size.). Further, although the source mirror gives a very good image at the center of the field, points at the edge of the source are aberrated, which adds to the basic image magnification. However, if positive focusing elements can be placed in proximity to the detectors, the magnification can be radically reduced, and the aberrations also reduced in absolute terms. In the instant systems, a compressed beam can improve the detection efficiency by a factor of four or more. Note that in view of the aberrated condition of the beam, it is not feasible for a simple lens to form a good image on the detector, but in fact since the objective is just to collect as many infrared radiation rays as possible, a good image is not required.

Figure 22:
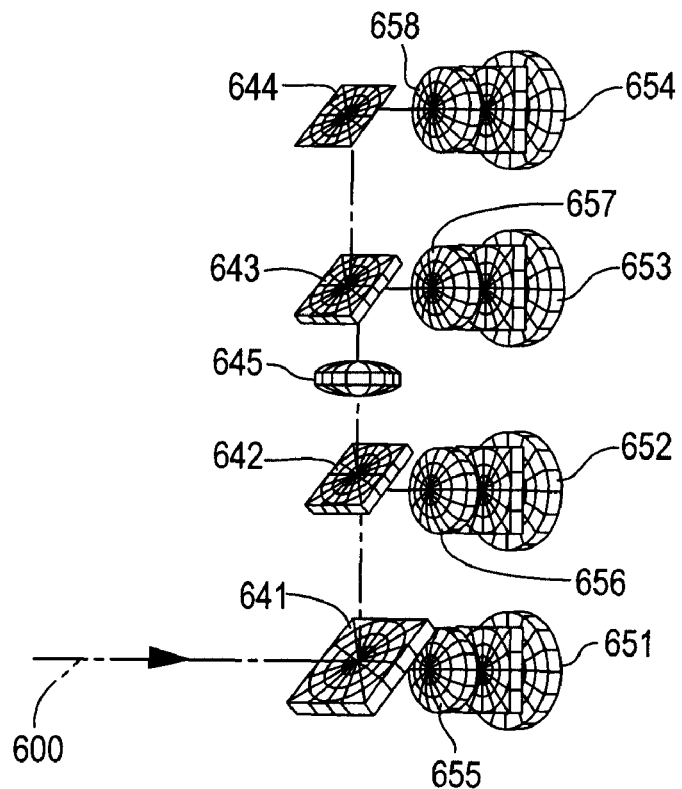
FIG. 22 is a schematic diagram of a four channel optical system in a linear system with lenses configuration.

FIG. 22 is schematic diagram of an optical system having a linear system configuration with lenses included in the optical assembly. This configuration is similar in layout to the linear configuration of FIG. 18, with the addition of a lens 645 inserted along the optical path, typically between beamsplitter 642 and 643 and filter/detector assemblies 652 and 653. The function of the lens is to compress the beam energy to detector assembly 653 and detector assembly 654, which will improve the efficiency of detection in those channels. The action of the lens is to reduce the magnification of the system. In addition, lenses 655-658 can be added to each channel, thereby reducing the magnification further, and improving and equalizing the efficiency of all detectors.

Figure 23:
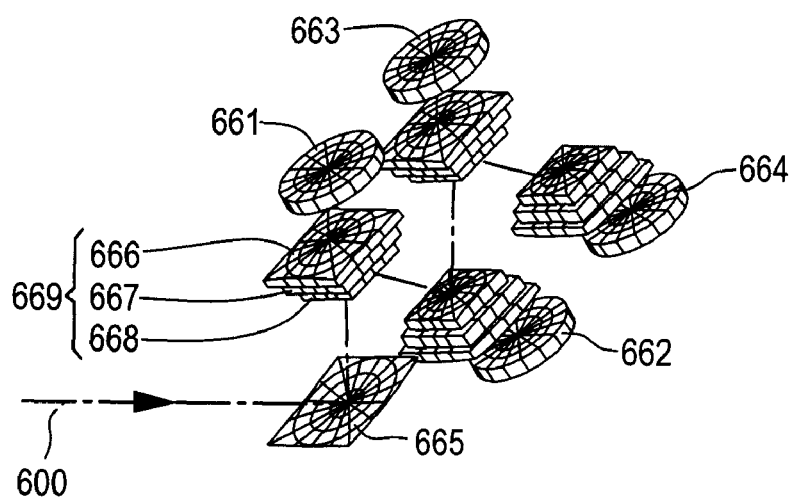
FIG. 23 is a schematic diagram of a four channel optical system in a zigzag with lenses configuration.

FIG. 23 is schematic diagram of an optical system having a zigzag configuration with lenses again included in the optical assembly. In this configuration, which is essentially a modification of that shown in FIG. 20, lenses are added at each channel to compress the beam size. If a single lens was added between the beam splitter and the detector, only the transmitted beam would be affected, and the reflected beam would expand more than desired by the last channel. But if a single lens is added in front of the beamsplitter that is strong enough to compress the beam suitably for that detector, the effect on the reflected beam would be doubled, and would be too strong.

The present invention solves this dilemma by splitting the lens into two components, one part on either side of a narrow bandpass filter. For example, split lens/filter assembly 669 comprises lens 666 and 668 and filter 667. By splitting the lens in this way at each channel, the part that is transmitted and the part that is reflected each gain the effect of a full lens. Alternatively, the two lenses at each channel can be different, so that for example the transmitted beam can be more strongly compressed as compared to the reflected beam. Note that with this system, the dichroic beam splitters are eliminated.

Figure 24:
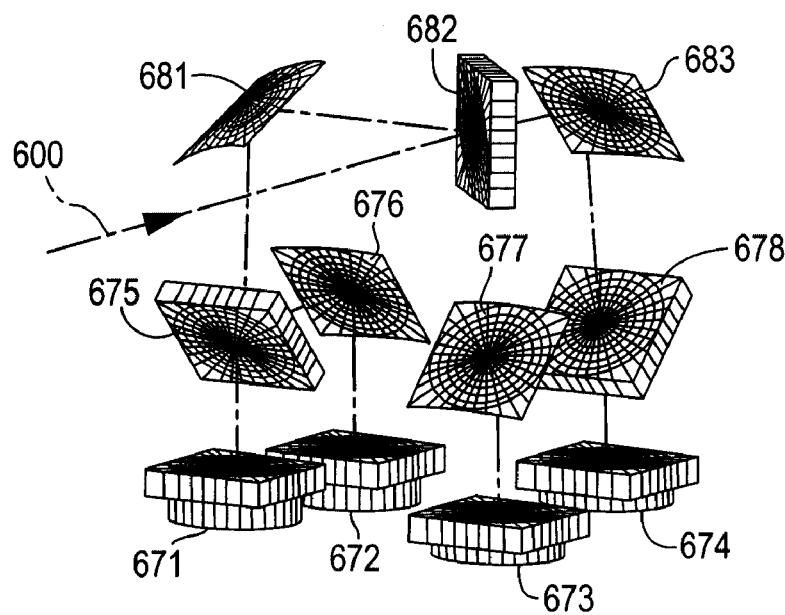
FIG. 24 is a schematic diagram of a four channel optical system in a dogleg configuration.

FIG. 24 is schematic diagram of an optical system having a dogleg configuration. This configuration is similar to the square array in that the dichroic beam splitters are used to split the beam by wavelengths in a binary manner. Dichroic beamsplitter 682 does the first division. The reflected beam goes to reflector 681. This is one of four focusing mirrors that are added to compress the beam to improve detection efficiency. These mirrors can be spherical, but, preferentially, they are aspherical. This preference arises because a spherical element at a high angle of incidence will produce two different focal points, one in the plane of incidence, the other perpendicular to that. In other words, such a mirror will produce an astigmatic image. By making the radius of curvature different in the two axes, the astigmatism can be corrected. Aspheric is a general term for a surface that is not spherical. The mirrors shown here are toroidal, a sub-set of the general class. In the present case, even though a good image is not required, an aspheric mirror can produce a more uniform circular beam pattern.

The reflected and re-focused beam is split again at dichroic beamsplitter 675. Again the reflected beam is re-focused on to the bandpass filter/detector assembly 672. The transmitted beam goes to filter/detector assembly 671. The transmitted beam from beamsplitter 682 is re-focused by focusing mirror 683, and split by beamsplitter 678. As with the other two channels, the beam goes to filter/detector assembly 674, or to filter/detector assembly 673 via focus mirror 677. Note that this system provides high collection efficiency, and a compact single-plane detector array.

Figure 25:
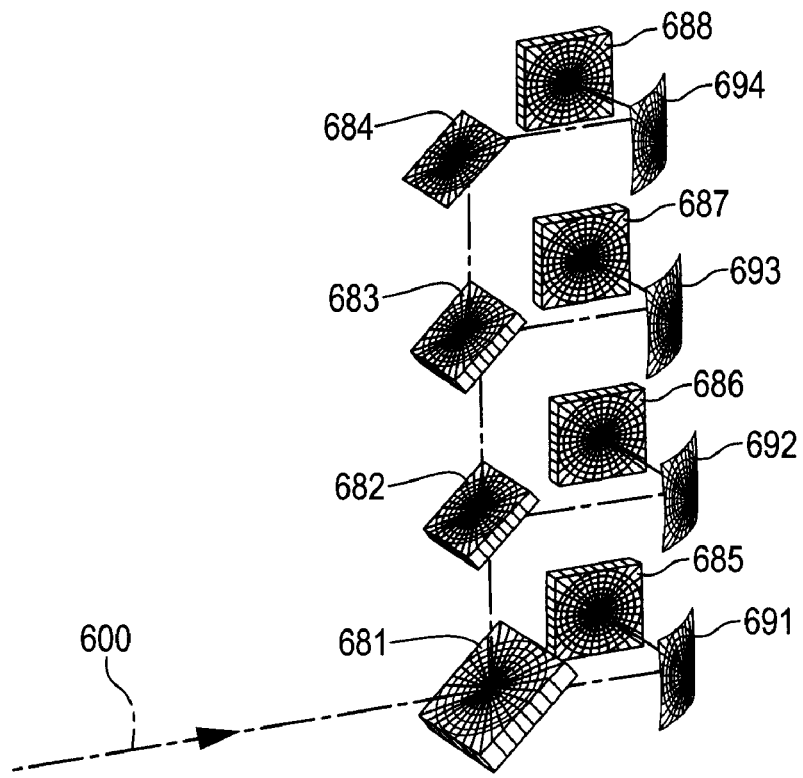
FIG. 25 is a schematic diagram of a four channel optical system in a snake configuration.

FIG. 25 is schematic diagram of an optical system having a snake configuration. The "snake" architecture is similar to the linear array, except that focusing mirrors 691-694 are added to each channel. The initial split is done by dichroic beamsplitter 681, followed by beamsplitters 682 and 683, and mirror 684. The focusing mirrors can be spherical, but aspherical mirrors make a significant improvement in collection efficiency. In an exemplary embodiment of the present invention, the mirrors are made in a single long molding. The filter/detector assemblies 685, 686, 687, and 688 consist of a narrow bandpass filter and detector, the same as in the other previously described embodiments.

Figure 26:
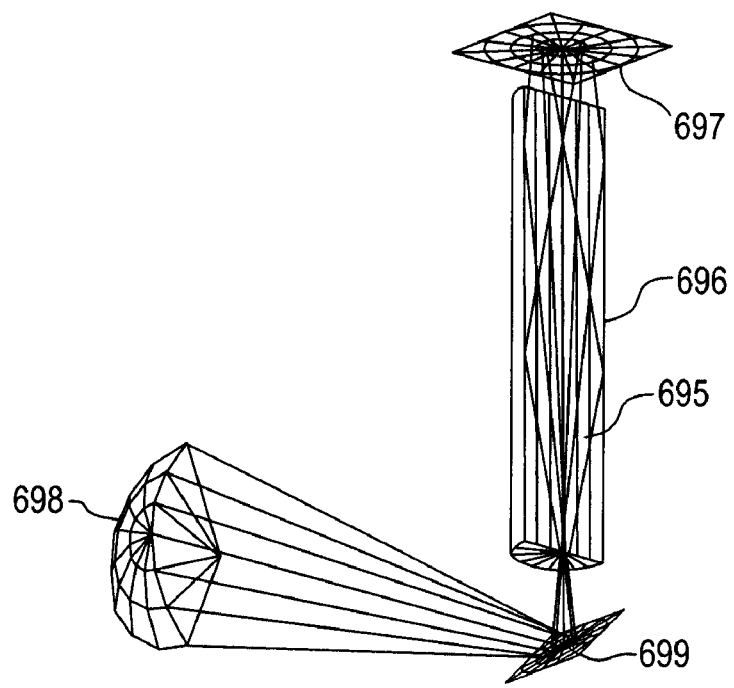
FIG. 26 is a schematic diagram of a four channel optical system in a tunnel configuration.

FIG. 26 is schematic diagram of an optical system having a tunnel configuration. Infrared energy can be distributed to a planar array of detectors in a different way. Energy from the source 698 can be directed into a pipe 696 by mirror 699, or what may be termed an optical tunnel. If an interior 695 of the pipe is a mirror, and if the pipe is long enough (of the order ten times the diameter), the energy at the end of the pipe will be well mixed, geometrically. That is, any structure in the input beam, for example, due to an imperfection in the airway, or a drop of liquid on an airway window, will not be detectable at the output (although the overall energy level may be down). Similarly, if the input beam is not exactly in the right place, or at the right angle, there will be essentially no effect at the output.

The idea of this embodiment to put a planar array 697 of narrow bandpass filters and associated detectors at the output. The action of the tunnel will distribute the energy symmetrically to the detectors. Note that the energy at the output is radially symmetric, but not uniform over the area. The system as described is not efficient, because the pipe output is circular, while the array is square (for four detectors), and further, the area of each detector is a fraction of the total output area. This loss in efficiency can be alleviated by making the pipe square to match the detector array, or alternatively, a set of funnels can be placed at the output. These funnels would, as a group, accept all of the energy from the pipe, divide it multiple ways to match the number of channels, and concentrate the energy down to the detector size. In the figure, the side of the pipe (and the source mirror) has been cut away for illustration. The detector plane does not show the array.

Figure 27:
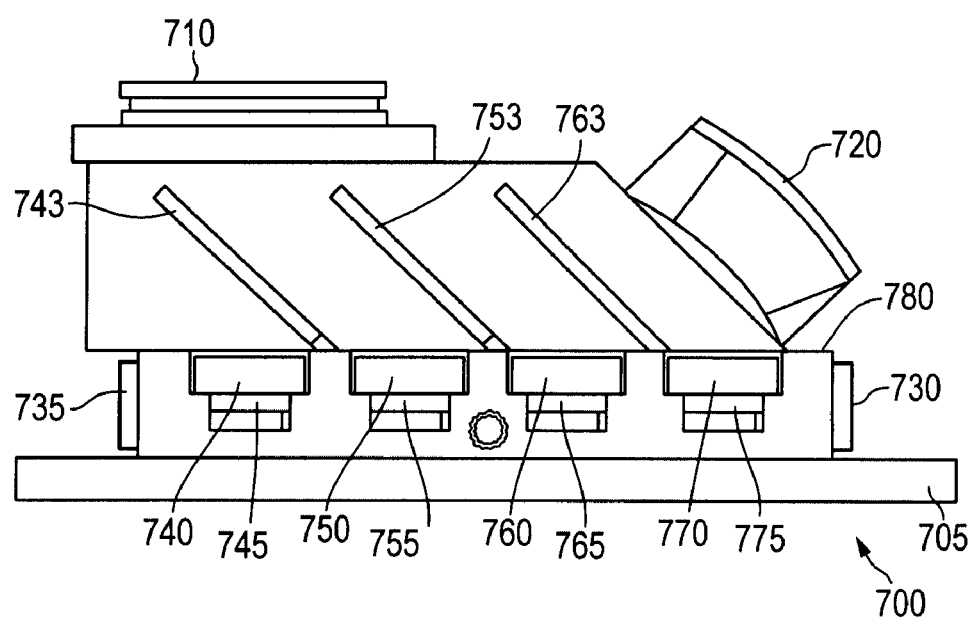
FIG. 27 is a side view of an embodiment of a four channel optical system in a linear configuration.

FIG. 27 is a side view of an embodiment of a four channel optical system 700 disposed in a linear configuration on a substrate 705. Infrared radiation enters detector/optical assembly 700 by first passing through lens 710. The infrared radiation is then successively split and reflected by beamsplitters 743, 753, and 763. The transmitted infrared radiation passes through filters 740, 750, and 760 prior to detectors 745, 755, and 765, respectively. The remaining infrared radiation that passes through beamsplitter 763 is reflected by focusing mirror 720 through filter 770 and onto detector 775. Heaters 735 and 730 serve to maintain the detector block 780 at a constant temperature.

In the above-described embodiments, multiple absorption type detector assemblies are provided to detect more than one gas constituent in the gas flowing in the sample cell. It is to be understood that the present invention also contemplates providing multiple gases for luminescence quenching type of gas detectors, either alone or in combination with the absorption type of detectors. Multiple luminescence quenching type of gas detectors would need multiple sources, detectors, with filters and multiple chemistries on the substrate of the airway adapter.

Figure 28:
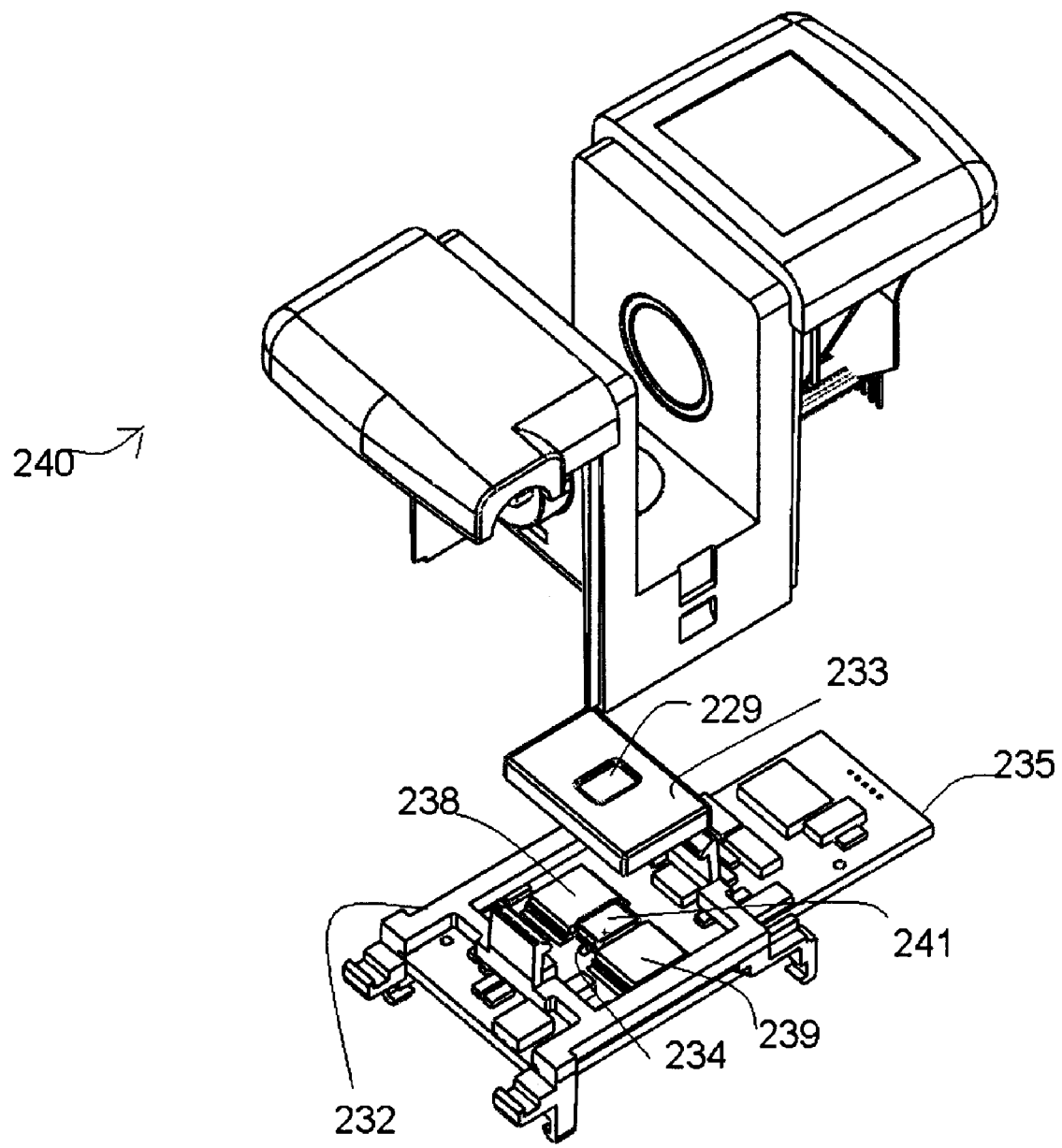
FIG. 28 is an exploded view of the a portion of the gas measurement system optical assembly according to the principles of the present invention.
Figure 29:
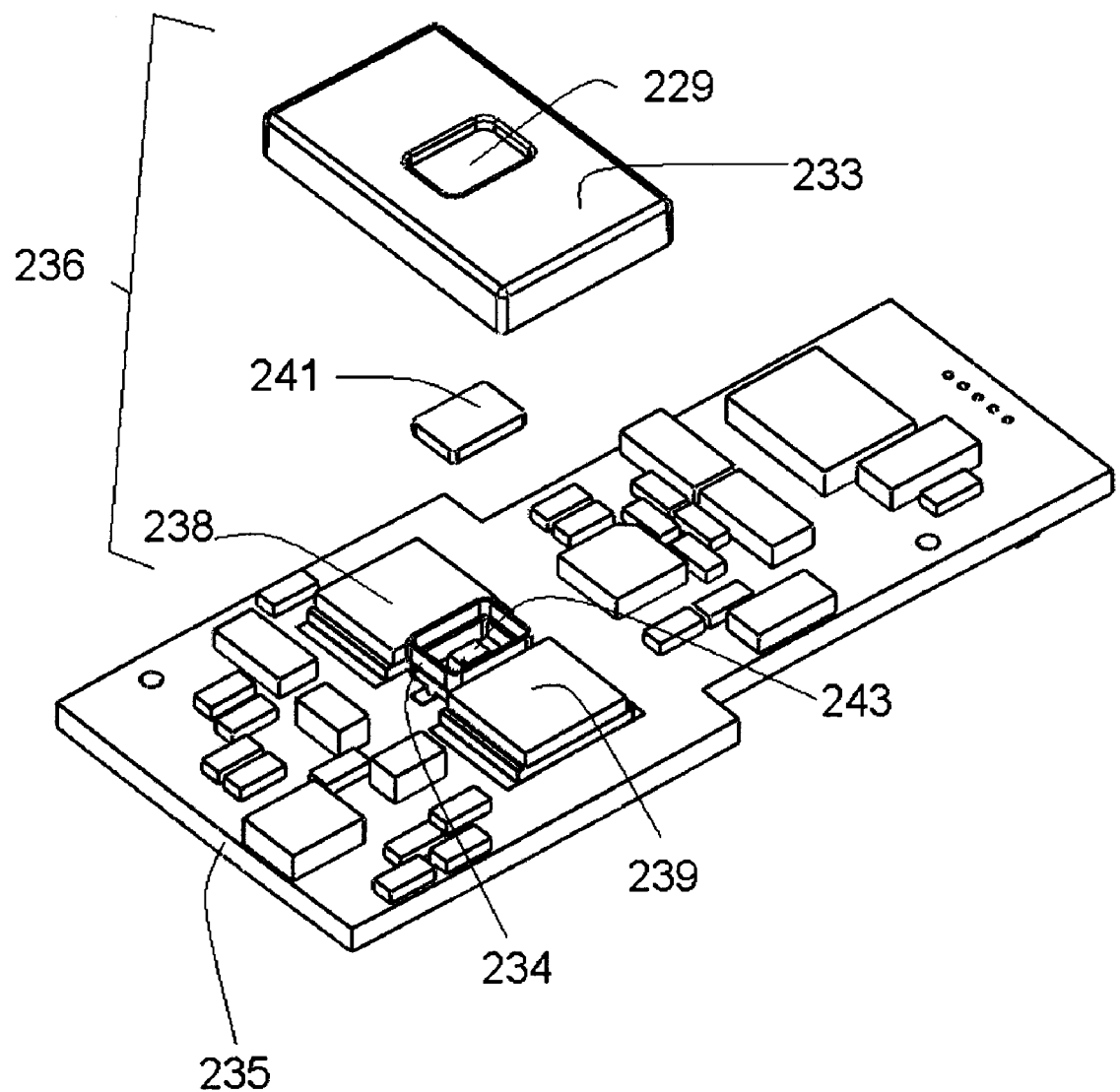
FIG. 29 is an exploded view of luminescence quenching measurement circuit board in the gas measurement system of FIG. 28.

FIG. 28 is a perspective exploded view of the gas measurement system optical assembly 240 and luminescence quenching measurement circuit board 235 with bracket 232. Detector filter 233 is shown in FIG. 29 removed from luminescence quenching optical system 236, which is assembled to luminescence quenching measurement circuit board 235. Luminescence quenching measurement circuit board 235 includes the circuitry to drive excitation source 243 and measure the response with detectors 238 and 239 using known detection techniques.

FIG. 29 is a perspective exploded view of luminescence quenching measurement circuit board. The exemplary luminescence quenching optical system 236 includes excitation source 243, detectors 238 and 239 positioned on each side of excitation source 243, detector filter 233, optional excitation source filter 241, and shield 234. All are disposed on the same plane permitting size and weight to be reduced. An exemplary excitation source consists of a green light emitting diode. Excitation source 243 and detectors 238 and 239 are separated from each other by electrical shielding and optical filters. An exemplary detector consists of a photodiode. It is to be understood that the present invention contemplates providing a ring of photodetectors surrounding or partially surrounding source 243. This ring can be a single detector or a plurality of detectors and can have any suitable pattern, such as circular, square, triangular, rectangular, etc.

Detector filter 233, in the exemplary embodiment, is a rectangular filter structure with an aperture 229 through which the radiation from the excitation source is emitted. The optical properties of detector filter are such that the wavelengths of radiation related to the luminescence quenching of the sensing film/chemistry in response to contact with the gas or gases to be measured are substantially transmitted through the filter and radiation not related to that interaction is substantially not transmitted through the filter. The detector filters may be bandpass, highpass, lowpass, or any other filter type known in the art. In addition, an optional excitation source filter 241 may be used to limit the emission of radiation outside the wavelengths of radiation to which the sensing film is excited by thereby preventing unwanted wavelengths from reaching the sensing film.

The sensing film that is sensitive to a gas of interest is preferably disposed on a plane that is parallel to, and displaced from, said first plane of the exemplary luminescence quenching optical system 236. To minimize unwanted interaction between the excitation source and detectors, shield 234 is placed around excitation source. The internal surface of shield 234 in the exemplary embodiment is substantially reflective for the radiation emitted by the excitation source thereby serving two purposes. This allows it to redirect the extraneous light back towards the sensing film improving the efficiency of the system Additionally, excitation sources, such as LEDs, emit light into a larger angle than that subtended by the sensing film. The shape of the shield is preferably designed to block the light from reaching the detectors directly and influencing the luminescence measurement.

In the exemplary embodiment shown, the radiation emitted from the excitation source 243 is transmitted through filter 241 and through the domed window 247 and is incident on the sensing film 248 (FIG. 14). Based on the concentration of oxygen, the sensing film emits radiation at a different wavelength which is transmitted back through window 247 and filtered by detector filter 233 and measured by the two detectors disposed within detector filter 233.

Additionally, index matching layer (not shown) may be optionally positioned between the detectors and detector filter to minimize reflective loss. Radiation from the sensing film is emitted in all directions and only a small fraction of the emitted radiation is directed towards the detectors. Due to fresnel reflections, this radiation is further attenuated at every interface along the optical path. Thus, filling the air gaps with a material, such as an index matching material, allows this reflective loss to be minimized.

Heater flex circuit 245 is electrically interfaced to luminescence quenching measurement circuit board 235 as noted above. Temperature control or compensation is required because the amount of luminescence emitted from the sensing film is influenced by temperature. To maintain a constant temperature at the film, window heater 245 thermally communicates to the flat side of the window 247 which conventionally is sapphire This heater keeps the window 247 at a constant temperature which in turn maintains the temperature of the sensing film. The window heater 245 is designed into a ring shape to remain outside of the optical path. Window 247 is domed instead of flat to improve thermal contact with the sensing film. The close contact between these two components and the curved profile also have the effect of improving the amount of light transmitted through to the sensing film and back towards the detectors. As noted above, an exemplary embodiment of a luminescence quenching optical system 236 suitable for use in the present invention is disclosed in the '451 application.

It is to be understood that the luminescence quenching feature of the present invention and the absorption feature of the present invention can be used alone or in combination and in a sidestream configuration as well.

A number of alternative structures for the invention are presently contemplated. For example, the present invention contemplates using a prismatic lens or aspheric lens in front of the excitation source to distribute light more uniformly over the sensing film. It is also contemplated interchanging the position of excitation source and detectors, i.e., use a single large detector that is surrounded by two or more excitation sources. The present invention further contemplated angling or tilting the detectors so that the detector face in substantially perpendicular to the radiation emitted from the luminescence material to improve detection efficiency.

The present invention also contemplates providing display 800 (see FIG. 3) on the housing of the gas measurement system. The display can be any suitable display, such as an LED, OLEDs, LCD, etc. Providing a display on the housing of the gas measurement system permits the clinician or other user to visualize warnings or advisory messages, waveforms, trends, and other relevant information directly from the unit proximate to the patient, without having to reposition themselves to see a conventional monitoring screen, which is typically necessary because in a conventional system the monitoring screen is often several feet away from the patient. This would be of particular importance during an adverse clinical event that would require the immediate attention and response of the clinician.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A gas measurement system assembly comprising:
   (a) a housing adapted to be mounted on an airway adapter; and
   (b) a luminescence quenching gas measurement assembly disposed in the housing, comprising:
      (1) a source with an emitting surface disposed in a first plane for providing incident radiation incident on a sensing film, and
      (2) a plurality of detectors having detecting surfaces also disposed in the first plane, wherein each of the detecting surfaces faces the sensing film in the airway adapter to receive direct radiation from the sensing film responsive to the incident radiation from the source.

2. The system of claim 1, wherein the plurality of detectors are disposed proximate to the source.

3. The system of claim 1, wherein the plurality of detectors include a first detector disposed on a first side of the source, and a second detector disposed on a second side of the source.

4. The system of claim 1, wherein the housing is generally U-shaped.

5. The system of claim 1, further comprising a processor disposed in the housing, wherein the processor is programmed to measure a gas constituent of a gas flow in the airway adapter based on an output of the plurality of detectors.

6. The system of claim 1, further comprising a filter over the plurality of detectors, wherein the filter passes wavelengths of radiation related to luminescence quenching and substantially blocks other wavelengths.

7. The system of claim 1, further comprising an optical shield disposed around at least a portion of the source.

8. The system of claim 1, further comprising an infrared absorption gas measurement assembly disposed in the housing.

9. The system of claim 8, wherein the housing has a generally U-shaped configuration having a first leg and a second leg, wherein the infrared absorption gas measurement assembly comprises a source assembly disposed in the first leg and a detector assembly disposed in the second leg, and wherein the luminescence quenching gas measurement assembly is disposed in the housing between the first leg and the second leg.

10. The system of claim 1, wherein the first plane is parallel to a sensing film in the airway adapter.

11. The system of claim 1, wherein the direct radiation from the sensing film is not reflected in paths between the sensing film and the plurality of detector.

12. A gas measurement system, comprising:
   (a) a conduit adapted to carry a flow of gas;
   (b) a sensing film in communication with the flow of gas in the conduit;
   (c) a luminescence quenching gas measurement assembly adapted to measure a constituent of the flow of gas, wherein the luminescence quenching gas measurement assembly comprises:
      (1) a radiation source with an emitting surface disposed in a first plane substantially parallel to the sensing film for providing incident radiation incident on the sensing film, and
      (2) a plurality of detectors having detecting surfaces also disposed in the first plane, wherein each of the detecting surfaces faces the sensing film to receive direct radiation from the sensing film responsive to the incident radiation from the radiation source.

13. The system of claim 12, further comprising an airway adapter selectively coupled to the conduit, wherein the sensing film is disposed on the airway adapter.

14. The system of claim 12, wherein the plurality of detectors are disposed proximate to the radiation source.

15. The system of claim 12, wherein the plurality of detectors include a first detector disposed on a first side of the radiation source, and a second detector disposed on a second side of the radiation source.

16. The system of claim 12, further comprising a housing adapted to be selectively coupled to the conduit, wherein the luminescence quenching gas measurement assembly is disposed in the housing.

17. The system of claim 16, further comprising a processor disposed in the housing, wherein the processor is programmed to measure a gas constituent of a flow of gas in the conduit based on an output of a detector of the plurality of detectors.

18. The system of claim 16, further comprising an infrared absorption gas measurement assembly disposed in the housing.

19. The system of claim 18, wherein the housing has a generally U-shaped configuration having a first leg and a second leg, wherein the infrared absorption gas measurement assembly comprises a source assembly disposed in the first leg and a detector assembly disposed in the second leg, and wherein the luminescence quenching gas measurement assembly is disposed in the housing between the first leg and the second leg.

20. The system of claim 12, further comprising a filter disposed over the plurality of detectors, wherein the filter passes wavelengths of radiation related to luminescence quenching and substantially blocks other wavelengths.

21. The system of claim 12, wherein the direct radiation from the sensing film is not reflected in paths between the sensing film and the plurality of detector.

* * * * *